「12」 United States Patent
Sasaki et al.

(10) Patent No.: US 6,950,549 B2
(45) Date of Patent: Sep. 27, 2005

(54) VISUAL INSPECTION METHOD AND VISUAL INSPECTION APPARATUS

(75) Inventors: Yoshihiro Sasaki, Tokyo (JP); Masahiko Nagao, Tokyo (JP)

(73) Assignee: NEC Electronics Corporation, Kanagawa (JP)

( * ) Notice: Subject to any disclaimer, the term of this patent is extended or adjusted under 35 U.S.C. 154(b) by 625 days.

(21) Appl. No.: 10/073,168

(22) Filed: Feb. 13, 2002

(65) Prior Publication Data

US 2002/0110271 A1 Aug. 15, 2002

(30) Foreign Application Priority Data

Feb. 14, 2001 (JP) ........................................ 2001-037497

(51) Int. Cl.$^7$ ................................................. G06K 9/00
(52) U.S. Cl. .......................... 382/145; 348/126; 700/110
(58) Field of Search ................................. 382/141–152; 348/86, 87, 125, 126; 700/95, 96, 108, 110

(56) References Cited

U.S. PATENT DOCUMENTS 5,408,538 A * 4/1995 Kitakado et al. ........... 382/145
6,167,149 A * 12/2000 Tsujikawa et al. .......... 382/147

FOREIGN PATENT DOCUMENTS

| JP | 8-203972   | 8/1996  |
| JP | 9-311014   | 12/1997 |
| JP | 2000-65543 | 3/2000  |
| JP | 2000-121338| 4/2000  |

* cited by examiner

Primary Examiner—Jon Chang
Assistant Examiner—Charles Kim
(74) Attorney, Agent, or Firm—Young & Thompson

(57) ABSTRACT

In a visual inspection method and apparatus, a picture processing unit converts an original picture, obtained by taking a photograph of a BGA illuminated by a ring illuminator from above, using a camera, and labels a binary picture obtained by this binary conversion. Then, it forms a rectangle circumscribing an outer circumference of a labeling picture obtained by the labeling, and inverts a labeling picture within the formed circumscribing rectangle, and removes a portion of a region formed by the outer circumference and the circumscribing rectangle in a picture obtained by the inversion, and then generates an inspection picture by adding a picture obtained by the removal to the labeling picture, and accordingly judges a pass or rejection of the inspection target sample based on the generated inspection picture. Thus, the inspection can be carried out at high accuracy irrespectively of a low cost.

8 Claims, 22 Drawing Sheets

40:CIRCUMSCRIBING RECTANGLE

40: CIRCUMSCRIBING RECTANGLE

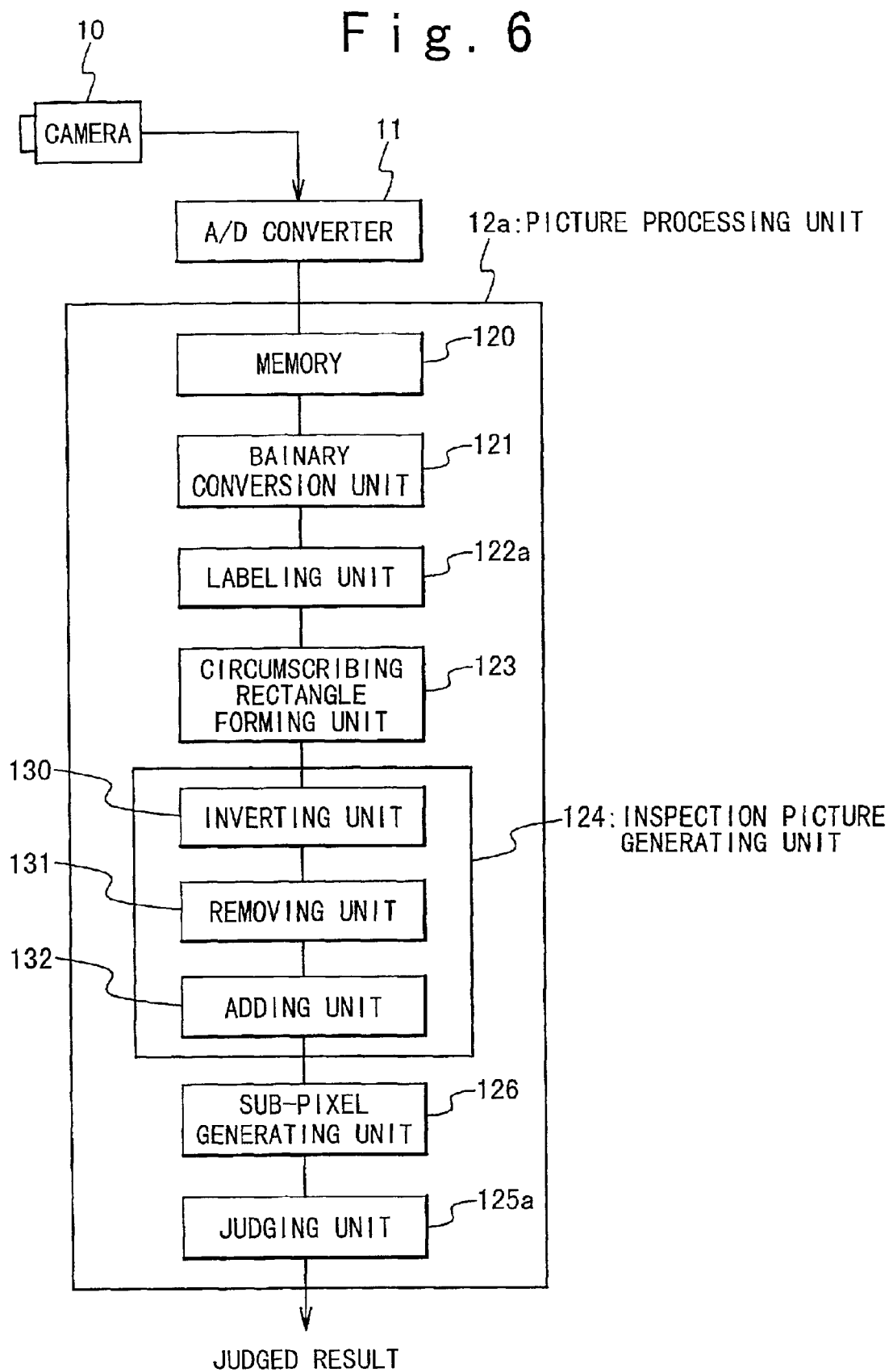

VISUAL INSPECTION METHOD AND VISUAL INSPECTION APPARATUS

BACKGROUND OF THE INVENTION

1. Field of the Invention

The present invention relates to a visual inspection method of and a visual inspection apparatus for performing a visual inspection on an inspection target sample by using an imaging process. More particularly, the present invention relates to a technique for minutely inspecting a shape of a protrusion of a BGA (Ball Grid Array).

2. Description of the Related Art

Conventionally, a visual inspection apparatus and a visual inspection method have been known for taking a photograph of an integrated circuit (IC) having a package of a BGA type, and then inspecting an appearance of the integrated circuit by using a picture obtained by this photograph operation.

As such a visual inspection apparatus, for example, Japanese Laid Open Patent Application (JP-A-Heisei 9-311014) discloses "Apparatus for Inspecting Protrusion of Semiconductor Integrated Circuit Apparatus". This apparatus for inspecting a protrusion compares a rough coordinate of a protrusion targeted for an inspection with a coordinate at which the protrusion should be originally existed. As this comparison result, if it is so judged that a position of the protrusion is largely deviated from a position defined by an inspection standard, a position deviation error signal is outputted. Then, the inspection of the protrusion is stopped, and the inspection of a next protrusion is executed. On the other hand, if it is judged that the protrusion is not largely deviated from the position defined by the inspection standard, a high accurate judgment of the position is requested.

In response to this request of the high accurate judgment of the position, a sub-pixel protrusion coordinate is compared with the coordinate at which the protrusion should be originally existed. Then, it is judged that a positional deviation error is occurred if the comparison result is not within a preset allowable range of a positional deviation. The above-mentioned process enables a positional deviation of a solder protrusion to be quickly inspected at a high accuracy.

Japanese Laid Open Patent Application (JP-A-Heisei 8-203972) discloses "Protrusion Inspecting Apparatus". In this protrusion inspecting apparatus, an inspection target surface is illuminated from a horizontal direction or an obliquely upward direction close to a horizontal direction, and a photograph of the inspection target surface is taken by using a camera placed above the inspection target surface. Then, a binary conversion process is performed on shade picture data obtained from the photograph operation, and a labeling process is performed on the binary converted shade picture data. As for a judgment of a pass or a rejection, in a first method, the number of labels having a region of a normal size is compared with the predetermined number of protrusions, and it is judged as the pass if they coincide with each other.

In a second method, a central coordinate of a label corresponding to a protrusion detected by the inspection in the last time is used as a start point. Then, a label of a next protrusion having a central coordinate at a coordinate separated by a predetermined distance from this start point is sequentially retrieved, and it is judged as the pass if labels corresponding to all protrusions are retrieved. Thus, it is possible to detect the defects such as a breaking and a size error of a protrusion formed by a solder ball on a BGA board, a bump on a semiconductor apparatus and the like.

As another related art, Japanese Laid Open Patent Application (JP-A 2000-65543) discloses "Bump Illuminating Method and Apparatus, Bump Photographing Method and Apparatus, Picture Processing Method and Apparatus, Bump Inspecting Method and Apparatus, And Information Storage Medium". In this technique, a solder bump is illuminated from all circumference directions, and a photograph of the solder bump is taken while a light amount at a center is reduced. The quality of a coating state of reinforcement resin on the solder bump is automatically inspected by extracting an object from the picture data obtained by the photograph operation, and then confirming an area and an aspect ratio. Thus, it is possible to easily inspect the quality of the spherical solder bump on which lower half the reinforcement resin is coated after the solder bump is mounted on a surface of a circuit board.

As still another related art, Japanese Laid Open Patent Application (JP-A 2000-121338) discloses "Apparatus for Inspecting Electronic Part". In this apparatus for inspecting the electronic part, a cylindrical illuminating unit is placed above a lens of a camera. Two ring-shaped light source rooms, each of which is constituted by three interiorly projected flanges, are formed in upper and lower two stages, in an upper opening portion of the illuminating unit. A light source composed of a plurality of LEDs is placed at each of their tips so that a ring-shaped illuminator is formed. A part retainer, such as a work head and the like, for a part loading apparatus, which is located close to the upper opening portion, retains a BGA electronic part at a tip of an adsorption nozzle, and waits for the photograph operation. The photograph of a bump having a normal shape taken by the camera is obtained as a ring-shaped optical picture having a uniform ring width and being continued in a dark background. The pass or rejection is judged by measuring a diameter of the optical picture and the width of the ring from an angle at which the optical image is divided into at least eight portions and then comparing with a preset data. According to this apparatus for inspecting the electronic part, it is possible to judge the pass or rejection of the bump of the BGA electronic part surely and quickly.

However, in each of the techniques disclosed in Japanese Laid Open Patent Application (JP-A-Heisei 9-311014) and Japanese Laid Open Patent Application (JP-A-Heisei 8-203972), the shade picture data captured by using the camera is converted into the binary numeral in a pixel unit. Then, the pass or rejection of the protrusion is judged based on the binary picture data obtained by the above conversion. Thus, the inspection accuracy depends on whether or not there are a large number of pixels in the binary picture data. Hence, there may be a case that a visual inspection apparatus using a cheap element for taking a photograph can not detect the shape defect. This results in a problem that the inspection accuracy is low.

SUMMARY OF THE INVENTION

Therefore, an object of the present invention is to provide a visual inspection method and a visual inspection apparatus that can carry out a visual inspection at a high accuracy irrespectively of a low cost.

Means for achieving the object will be described below using reference numerals and symbols used in "Embodiments of the invention". These reference numerals and symbols are added so that relation between the description of "Scope of the Patent to be claimed" and the description of "Embodiments of the invention" is made clear. However, it is never permitted to use the reference numerals and symbols for the interpretation of technical scopes of the inventions described in "Scope of the Patent to be claimed" and the description of "Embodiments of the invention".

In order to attain the above-mentioned object, a visual inspection method according to a first aspect of the present invention is designed so as to take a photograph of an illuminated inspection target sample from above to generate an original picture, convert the original picture obtained by the taking into a binary picture, label the binary picture obtained by the converting to generate a labeling picture, form a circumscribing rectangle circumscribing an outer circumference of the labeling picture obtained by the labeling, invert the labeling picture circumscribed by the circumscribing rectangle formed by the forming to generate a inversion picture, remove a picture in a region surrounded by the outer circumference of the labeling picture and the circumscribing rectangle from the inversion picture obtained by the inverting to generate a removal picture, add the removal picture obtained by the removing to the labeling picture to generate an inspection picture and judge a pass or rejection of the inspection target sample based on the inspection picture obtained by the adding.

The visual inspection method according to the first aspect of the present invention is suitable for the judgment with regard to the pass or rejection of the inspection target sample, based on the binary picture having a hollow portion such as donut shape (a portion of a hole of a donut) obtained by, for example, taking a photograph of a spherical inspection target sample and converting into a binary numeral. It should be noted that, in this specification, the hollow portion implies the region of the existence of pixels having a value "0" surrounded with pixels having a value "1", and the portion of the hole of the donut shape corresponds to the hollow portion. The size of the hollow portion of the binary picture as mentioned above is typically is changed depending on the shape of the inspection target sample. Hence, it has the influence on inspection accuracy.

However, in the visual inspection method according to the first aspect of the present invention, the inspection picture where the same value as the binary numeral of the outer circumference of the binary picture is embedded in the hollow portion is used to judge the pass or rejection of the inspection target sample. Thus, the inspection independent of the size of the hollow portion can be done to thereby improve the inspection accuracy of the inspection target sample. It should be noted that the application of the visual inspection method according to the first aspect of the present invention is not limited to the case in which the binary picture of the inspection target sample is donut-shaped. Naturally, it can be applied to various binary pictures having the hollow portion.

In the visual inspection method according to the first aspect of the present invention, the judging step may perform judgement based on at least one of an area of the inspection picture, a diameter of the inspection picture and a circulation degree defined by a ratio of the area to another area calculated by a predetermined equation.

Also, in the visual inspection method according to the first aspect of the present invention may further comprises step of generating a new inspection picture by converting pixels around a plurality of pixels forming an outer circumference of the inspection picture into sub-pixels, and wherein the judging is performed based on the new inspection picture obtained by the generating. It should be noted that, in this specification, the following technique is referred to as a sub-pixel conversion. That is, with regard to concentration values of two pixels adjacent to each other, it calculates the rate at which the intended threshold level value is equivalent to the middle part of the two pixel values. Then, based on the rate, a division position between the two pixels is also divided at the same ratio as the rate. Then, an inner side is defined as "1", and an outer side is defined as "0". So, a line drawing is determined at a unit of a value less than one pixel.

According to this configuration, the outer circumference of the inspection picture is converted into the sub-pixels. Thus, the inspection picture having the high accuracy can be obtained to thereby improve the inspection accuracy. Also, the range for the sub-pixel conversion does not contain the entire inspection picture. It contains only the pixels in circumference of the plurality of pixels forming the outer circumference of the inspection picture. Hence, the sub-pixel conversion can be done at the high speed.

In order to attain the above-mentioned object, a visual inspection method according to a second aspect of the present invention is designed so as to take a photograph of an illuminated inspection target sample from above to generate an original picture, convert the original picture obtained by the taking into a binary picture, label the binary picture obtained by the converting to generate a labeling picture, calculate a summation of shade values of the original picture corresponding to the labeling picture generated by the labeling and judge a pass or rejection of the inspection target sample based on the summation of the shade values obtained by the calculating.

In order to attain the above-mentioned object, a visual inspection method according to a third aspect of the present invention is designed so as to take a photograph of an illuminated inspection target sample from above to generate an original picture, convert the original picture obtained by the taking into a binary picture, label the binary picture obtained by the converting to generate a labeling picture calculate a distance between every two pixels of a plurality of pixels forming an outer circumference of the labeling picture over all combinations of two pixels of the plurality of pixels, determine a longest distance of a plurality of the distances obtained by the calculating, and judge a pass or rejection of the inspection target sample based on the determined longest distance.

In order to attain the above-mentioned object, a visual inspection apparatus according to a fourth aspect of the present invention comprises a camera (10), a binary conversion unit (121), a labeling unit (122), a circumscribing rectangle forming unit (123), an inspection picture generating unit (124) and a judging unit (125).

The camera (10) takes a photograph of an inspection target sample illuminated with an illuminator (13) from above to output an original picture. The binary conversion unit (121) converts the original picture outputted from the camera (10) into a binary picture. The labeling unit (122) labels the binary picture outputted from the binary conversion unit (121) to generate a labeling picture. The circumscribing rectangle forming unit (123) forms a circumscribing rectangle circumscribing an outer circumference of the labeling picture generated by the labeling unit (122). The inspection picture generating unit (124) generates an inspection picture based on the labeling picture surrounded by the circumscribing rectangle formed by the circumscribing rectangle forming unit (123). The judging unit (125) judges a pass or rejection of the inspection target sample based on the inspection picture generated by the inspection picture generating unit (124).

The inspection picture generating unit comprises an inverting unit (130), a removing unit (131) and an adding unit (132). The inverting unit (130) inverts the labeling picture circumscribed by the circumscribing rectangle formed by the circumscribing rectangle forming unit (123) to generate a inversion picture. The removing unit (131) removes a picture in a region surrounded by the outer circumference and the circumscribing rectangle from the inversion picture generated by the inverting unit (130) to generate a removal picture. The adding unit (132) adds the removal picture generated by the removing unit (131) to the labeling picture to generate the inspection picture.

In order to attain the above-mentioned object, a visual inspection apparatus according to a fifth aspect of the present invention comprises a camera (10), a binary conversion unit (121), a labeling unit (122), a shade value summation calculation unit (140) and a judging unit (125b).

The camera (10) takes a photograph of an inspection target sample illuminated with an illuminator (13) from above to output an original picture. The binary conversion unit (121) converts the original picture outputted from the camera (10) into a binary picture. The labeling unit (122) labels the binary picture outputted from the binary conversion unit (121) to generate a labeling picture. The shade value summation calculation unit (140) calculates a summation of shade values of the original picture corresponding to the labeling picture generated by the labeling unit (122). The judging unit (125b) judges a pass or rejection of the inspection target sample based on the summation of the shade values calculated by the shade value summation calculation unit (140).

In order to attain the above-mentioned object, a visual inspection apparatus according to a sixth aspect of the present invention comprises a camera (10), a binary conversion unit (121), a labeling unit (122), a distance calculation unit (150) a longest distance calculation unit (151) and a judging unit (125c).

The camera (10) takes a photograph of an inspection target sample illuminated with an illuminator (13) from above to output an original picture. The binary conversion unit (121) converts the original picture outputted from the camera (10) into a binary picture. The labeling unit (122) labels the binary picture outputted from the binary conversion unit (121) to generate a labeling picture. The distance calculation unit (150) calculates a distance between every two pixels of a plurality of pixels forming an outer circumference of the labeling picture generated by the labeling unit (122) over all combinations of two pixels of the plurality of pixels. The longest distance calculation unit (151) determines a longest distance of a plurality of the distances calculated by the distance calculation unit (150). The judging unit (125c) judges a pass or rejection of the inspection target sample based on the longest distance determined by the longest distance calculation unit (151).

BRIEF DESCRIPTION OF THE DRAWINGS

FIG. 6 is a block diagram showing a configuration of a picture processing unit applied to a visual inspection apparatus according to a second embodiment of the present invention;

DESCRIPTION OF THE PREFERRED EMBODIMENTS

Now, embodiments of the present invention will be described below in detail with reference to the attached drawings.

Figure 1:
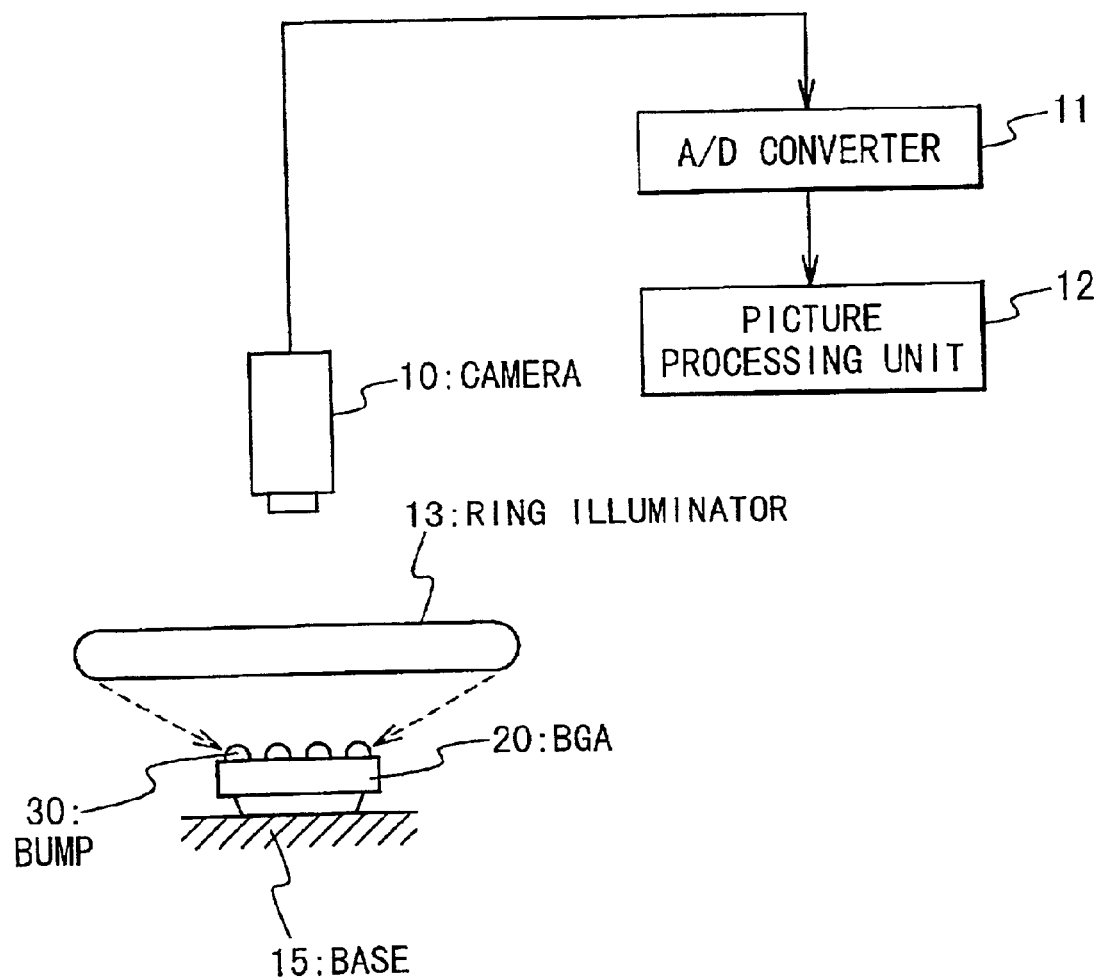
FIG. 1 shows a schematic configuration of a visual inspection apparatus according to each embodiment of the present invention.

FIG. 1 shows a schematic configuration of a visual inspection apparatus commonly used in each of the embodiments according to the present invention. This visual inspection apparatus is composed of a camera 10, an A/D converter 11, a picture processing unit 12, a ring illuminator 13 and a base 15 on which an integrated circuit 20 having a package of a BGA type (hereafter, merely referred to as "BGA") is mounted.

The camera 10 takes a photograph of the BGA 20 that is an inspection target sample. This camera 10 is placed so as to be located substantially directly over the BGA 20. An analog picture signal generated by taking the photograph operation of the camera 10 is sent to the A/D converter 11 for each pixel.

The A/D converter 11 converts the analog picture signal from the camera 10 into a digital picture signal for each pixel. Each pixel is composed of, for example, eight bits, and it is designed so as to indicate the shade values of 256 stages. The digital picture signal outputted from this A/D converter 11 is sent to the picture processing unit 12. It should be noted that the picture formed based on this digital picture signal is referred to as "original picture" in this specification.

The picture processing unit 12 can be configured by a computer having a processor, for example, such as a micro computer and a work station. This picture processing unit 12 treats the inputted digital picture signal to thereby perform a visual inspection on the BGA 20. The picture processing unit 12 will be described below in detail.

The ring illuminator 13 is composed of, for example, a ring-shaped fluorescent. This ring illuminator 13 is placed so as to be located substantially directly over the BGA 20, and it emits a light from an obliquely upward direction to the BGA 20 placed on the base 15.

A plurality of bumps 30 functioning as connection terminals are formed on a rear of the BGA 20. Each of the bumps 30 is constituted by, for example, a hemisphere-shape solder ball.

In the visual inspection apparatus having the above-mentioned configuration, a photograph of the rear of the BGA 20 where light is irradiate by the ring illuminator 13, is taken by the camera 10. Thus, a picture in which the plurality of bumps 30 are arrayed is obtained by the camera 10. In this case, the obtained picture of each of the plurality of the bumps 30 is donut-shaped. The principle by which the donut-shaped picture is obtained is explained in, for example, Japanese Laid Open Patent Application (JP-A-Heisei 8-203972). Refer to it as necessary.

The analog picture signal obtained by this camera 10 is converted into the digital picture signal by the A/D converter 11, and the converted digital picture signal is sent to the picture processing unit 12. The picture processing unit 12 treats the picture in which the plurality of donut-shaped bumps are arrayed, and inspects the outer appearances of the plurality of the bumps 30, and then judges the pass or rejection thereof.

The embodiments of the present invention will be described below. In this description, the configuration and the operation of the picture processing unit 12 is mainly explained.

(First Embodiment)

Figure 2:
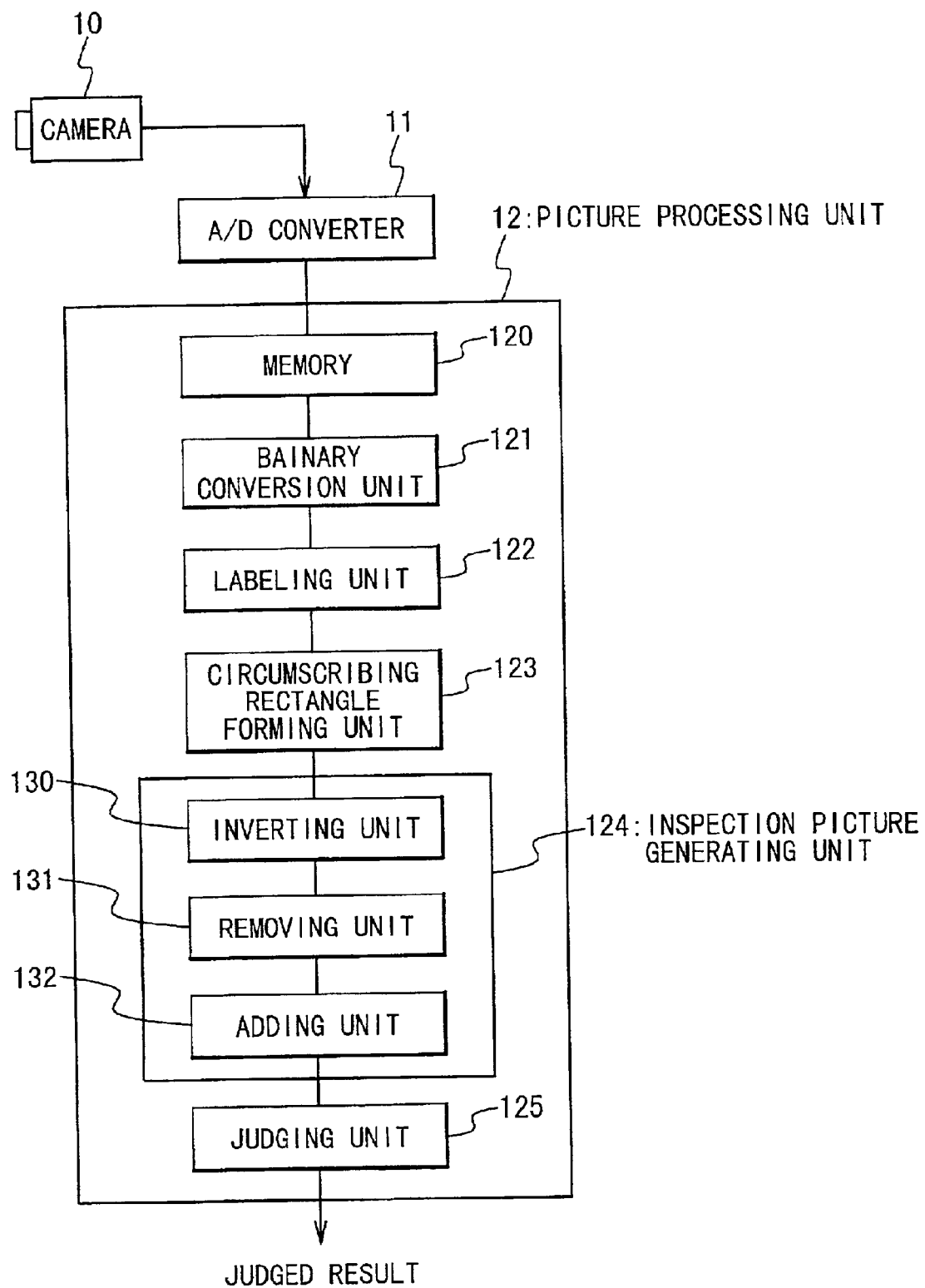
FIG. 2 is a block diagram showing a configuration of a picture processing unit applied to a visual inspection apparatus according to a first embodiment of the present invention.

FIG. 2 is a block diagram showing the configuration of the picture processing unit 12 applied to a visual inspection apparatus according to the first embodiment of the present invention.

The picture processing unit 12 is composed of a memory 120, a binary conversion unit 121, a labeling unit 122, a circumscribing rectangle forming unit 123, an inspection picture generating unit 124 and a judging unit 125.

The memory 120 stores therein the digital picture signal from the A/D converter 11 as digital picture data. The digital picture data stored in this memory 120 composes the original picture. The digital picture data stored in this memory 120 is sent to the binary conversion unit 121. It should be noted that the memory 120 is additionally used as temporal buffers for the binary conversion unit 121, the labeling unit 122, the circumscribing rectangle forming unit 123, the inspection picture generating unit 124 and the judging unit 125.

The binary conversion unit 121 converts the digital picture data stored in the memory 120 into the binary numeral. This binary conversion is carried out as follows. That is, the binary conversion unit 121 investigates whether or not a shade value of each pixel forming the digital picture data is equal to or greater than a predetermined threshold. If the shade value is equal to or greater than the threshold, the pixel is converted into "1". If the shade value is less than the threshold, the pixel is converted into "0". The binary picture data, which is converted into the binary numeral by this binary conversion unit 121, is sent to the labeling unit 122.

The labeling unit 122 extracts a region in which the pixels having the value "1" are continuous in the binary picture data sent from the binary conversion unit 121. This process is referred to as "labeling", and each labeled picture is referred to as "labeling picture". The labeling unit 122 sends the labeling picture obtained by the labeling to the circumscribing rectangle forming unit 123.

The circumscribing rectangle forming unit 123 forms the rectangle circumscribing an outer circumference of the labeling picture sent by the labeling unit 122. Hereafter, this rectangle is referred to as "circumscribing rectangle". An inner portion of the formed circumscribing rectangle serves as a unit of a picture processing in this visual inspection apparatus. The circumscribing rectangle data defining the circumscribing rectangle formed by this circumscribing rectangle forming unit 123 is sent to the inspection picture generating unit 124.

The inspection picture generating unit 124 inverts the labeling picture in the circumscribing rectangle defined by the circumscribing rectangle data sent from the circumscribing rectangle forming unit 123, and removes a portion of the region formed by the outer circumference of the labeling picture and the circumscribing rectangle from the picture generated by this inversion, and then adds the picture obtained by this removal to the labeling picture, and accordingly generates an inspection picture.

This inspection picture generating unit 124 is actually composed of an inverting unit 130, a removing unit 131 and an adding unit 132.

The inverting unit 130 inverts the labeling picture in the circumscribing rectangle to generate an inversion picture. That is, if a pixel which composes the labeling picture is at "0", the inverting unit 130 converts the pixel into "1", and if the pixel is at "1", the inverting unit 130 converts the pixel into "0", respectively. The inversion picture generated by inverting the labeling picture in the inverting unit 130 is sent to the removing unit 131.

The removing unit 131 removes a portion circumscribing the circumscribing rectangle from the inversion picture sent from the inverting unit 130. Actually, each pixel in a region formed by the outer circumference of the labeling picture and the circumscribing rectangle at each corner of the circumscribing rectangle is set to "0". The picture after the execution of the removing process in the removing unit 131 is sent to the adding unit 132.

The adding unit 132 adds the labeling picture in the circumscribing rectangle labeled by the labeling unit 122 and the picture after the execution of the removing process in the removing unit 131. This addition generates the inspection picture in which "1" is embedded in a hollow portion of the labeling picture. The inspection picture generated by the adding unit 132 is sent to the judging unit 125.

The judging unit 125 inspects the inspection picture sent from the adding unit 132 of the inspection picture generating unit 124, and judges the pass or rejection of the inspection of the BGA 20. This inspection in the judging unit 125 is carried out by calculating an area of the inspection picture and then inspecting whether or not the calculated result is within a predetermined range. The calculation of the area is carried out by counting the number of the pixels having the value "1" in the inspection picture The judged result by the judging unit 125 is sent to, for example, an external display apparatus (not shown).

The pass or rejection in the judging unit 125 may be done by investing whether or not a diameter of the inspection picture is within a predetermined range or whether or not a circulation degree of the inspection picture is within a predetermined range. This judgment of the pass or rejection may be also done by investigating whether or not at least one of the area, the diameter and the circulation degree of the inspection picture is within the predetermined range.

It should be noted that "circulation degree" in this specification indicates the degree close to the circulation which degree is represented by using a ratio of an area calculated based on the number of dots having a value equal to or greater than a threshold for the binary conversion in the inspection picture to another area calculated by following equation (1).

$$(\text{Maximum Diameter of Shape of Inspection Picture}/2)^2 \times \text{Circular Constant} \qquad \text{equation (1)}$$

The circulation degree is typically represented by a ratio of a length obtained from the number of the dots forming the outer circumference of the shape of the inspection picture to another length calculated from "Maximum Diameter of Shape of Inspection Picture ×Circular Constant". However, this typical circulation degree has a defect that if the shape of the inspection picture is distorted, the degree of the circulation can not be precisely represented. On the contrary, in the case of the circulation degree defined in this specification, the degree of the circulation can be precisely represented even if the shape of the inspection picture is distorted. Moreover, in the picture of the bump 30 having a crushed portion, the number of the dots having high brightness is dropped and thereby the circulation degree is reduced. Thus, this is advantageous in terms of detecting the bump 30 having the crushed portion.

Also, it is not always necessary that the inspection picture generating unit 124 is composed of the inverting unit 130, the removing unit 131 and the adding unit 132. This inspection picture generating unit 124 can employ the various configurations by which "1" can be embedded in the hollow portion of the labeling picture. For example, the inspection picture generating unit 124 can be configured such that all the pixels existed within the outer circumference of the labeling picture are converted into "1".

Figure 3:
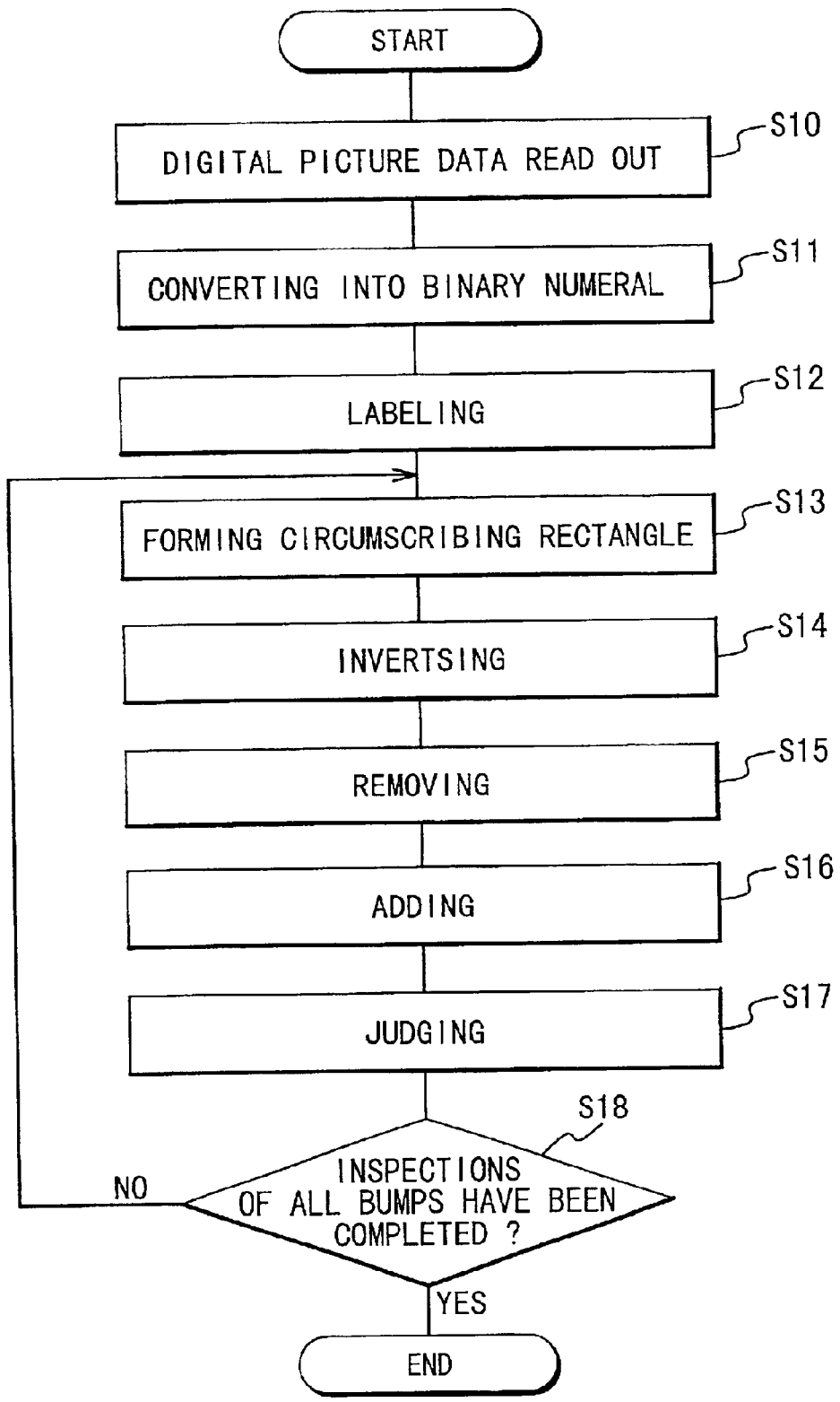
FIG. 3 is a flowchart showing an operation of the visual inspection apparatus according to the first embodiment of the present invention.

Next, the operation of the visual inspection apparatus according to the first embodiment of the present invention to which the picture processing unit 12 having the above-mentioned configuration is applied will be described below with reference to the flowchart shown in FIG. 3 and the explanatory diagram shown in FIG. 4.

At first, the BGA 20 that is the inspection target sample is placed on the base 15, and the ring illuminator 13 is turned on. Thus, the light is irradiated from the obliquely upward direction to the BGA 20 placed on the base 15. At this state, the camera 10 is actuated to then take a photograph of an entire of the BGA 20. The analog picture signal obtained by this photograph operation is converted into the digital picture signal by the A/D converter 11, as mentioned above, and the digital picture signal is stored as the digital picture data in the memory 120 of the picture processing unit 12. At this state, the picture processing unit 12 starts the operation.

In the picture processing unit 12, at first, the binary conversion unit 121 reads out the digital picture data from the memory 120 (Step S10), and then converts the read digital picture data into the binary numeral (Step S11). As the result of the binary conversion, the binary picture data is obtained in which the plurality of donut-shaped pictures corresponding to the plurality of bumps 30 are arrayed. This binary picture data is sent to the labeling unit 122.

Figure 4A:
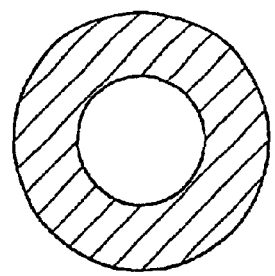
FIGS. 4A to 4E are explanatory diagrams describing the operation of the visual inspection apparatus according to the first embodiment of the present invention.

The labeling unit 122 executes a labeling process in which the binary picture data is labeled (Step S12). Thus, the plurality of labeling pictures corresponding to the plurality of the bumps 30 are obtained. Each of the labeling picture is donut-shaped as shown in FIG. 4A, unless the bump is extremely deformed. It should be noted that, in FIG. 4A, a slant portion indicates the pixels having the value "1", and the other portion implies the pixels having the value "0". Hereafter, they are similarly indicated.

Figure 4B:
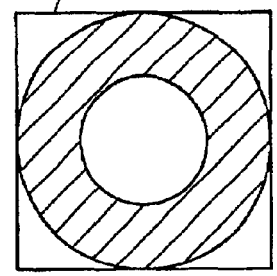

After the execution of this labeling process, the plurality of the labeling pictures corresponding to the plurality of the bumps 30 are treated one by one. That is, the circumscribing rectangle forming unit 123 selects one labeling picture from the plurality of labeling pictures sent from the labeling unit 122, as shown in FIG. 4B, and then generates a circumscribing rectangle 40 of the selected labeling picture (Step S13). The circumscribing rectangle data representing this generated circumscribing rectangle 40 is sent to the inverting unit 130 of the inspection picture generating unit 124.

Figure 4C:
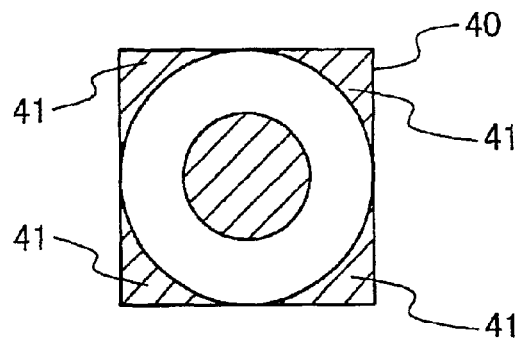

The inverting unit 130 inverts the labeling picture existed within a circumscribing rectangle defined by the circumscribing rectangle data from the circumscribing rectangle forming unit 123 (Step S14). Thus, an inversion picture shown in FIG. 4C is obtained.

The removing unit 131 removes portions 41 in contact with the circumscribing rectangle 40 of the inversion picture sent from the inverting unit 130 (Step S15). Thus, a removal picture having a donut-shaped hollow portion is obtained as shown in FIG. 4D.

Figure 4D:
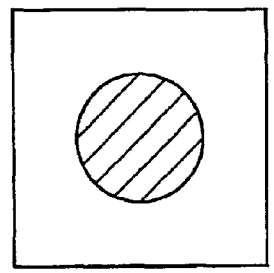
Figure 4E:
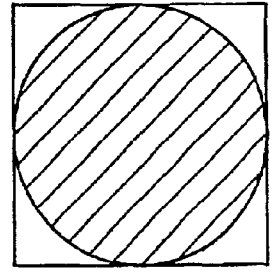

The adding unit 132 adds the labeling picture obtained by the labeling unit 122 as shown in FIG. 4B and the removal picture having the donut-shaped hollow portion sent from the removing unit 131 as shown in FIG. 4D (Step S16). Thus, the inspection picture in which all pixels existed within the outer circumference of the labeling picture are set to "1" is obtained as shown in FIG. 4E.

Then, the pass or rejection of the bump 30 that is the inspection target sample is judged (Step S17). More detailed, at this step S17, it is investigated whether or not an area of the inspection picture is within the predetermined range, and the pass or rejection is judged based on this investigation result. The judged result by the judging unit 125 is sent to, for example, an external display apparatus (not shown) and displayed thereon.

Next, it is investigated whether or not the inspections of all the bumps 30 have been completed (Step S18). If it is judged that the inspections have not been completed, the operational flow returns back to the step S13, and the above-mentioned processes are carried out, repeatedly. If it is judged at the step S18 that the inspections of all the bumps 30 have been completed, the visual inspection of one BGA 20 has completed.

The difference between the visual inspection apparatus according to the first embodiment of the present invention having the above-mentioned configuration and the conventional visual inspection apparatus will be described.

Figure 5A:
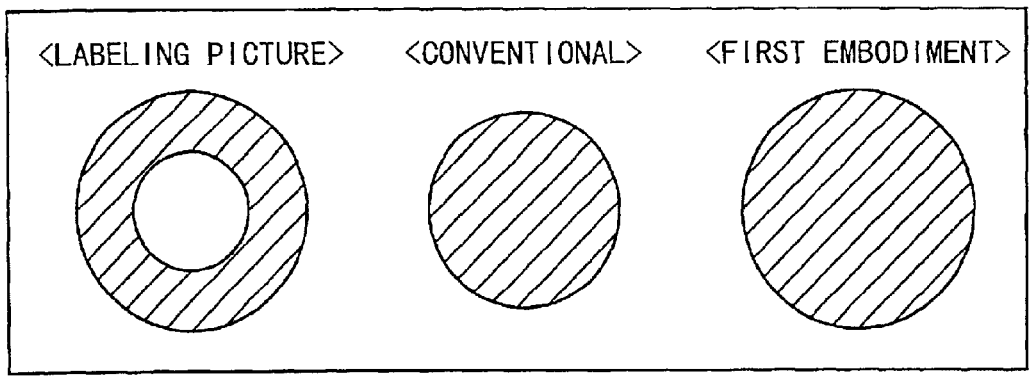
FIGS. 5A to 5C are explanatory diagrams describing a processed result by the visual inspection apparatus according to the first embodiment of the present invention, as compared with a conventional visual inspection apparatus.
Figure 5B:
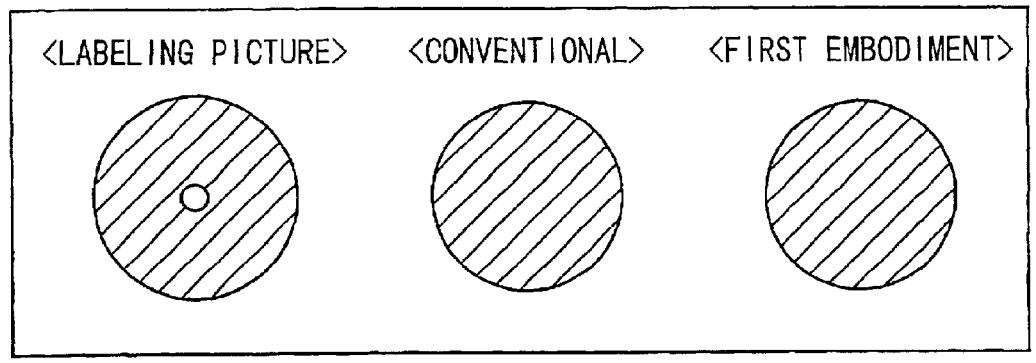
Figure 5C:
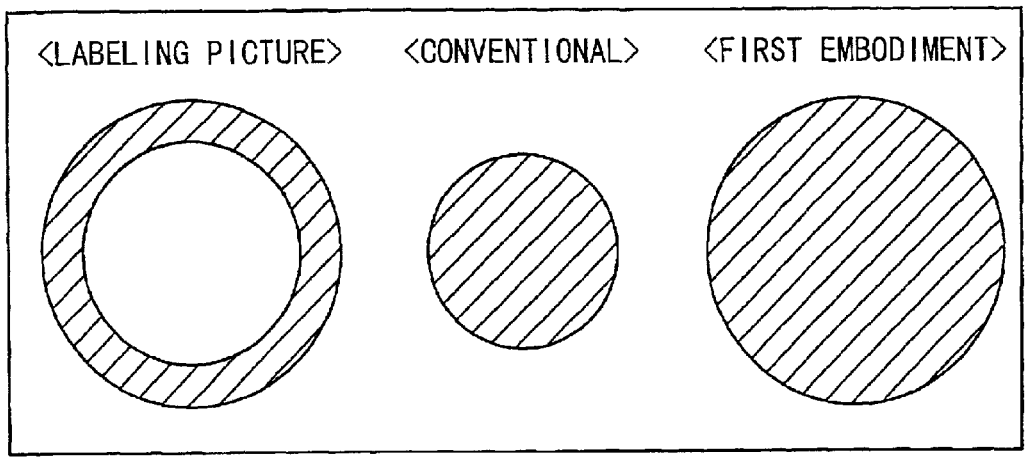

The shape of the labeling picture is determined depending on the appearance of the bump 30. Here, let us suppose that the labeling picture shown in FIG. 5A is normal and the labeling pictures shown in FIGS. 5B and 5C are abnormal. In the conventional visual inspection apparatus for judging the pass or rejection of the inspection based on the area of the labeling picture, all of the labeling pictures shown in FIGS. 5A, 5B and 5C have the same area, although the shapes of the labeling pictures are different from each other. As a result, such a case is occurred that the abnormal bump is judged to be normal. Thus, the pass or rejection of the inspection can not be precisely judged.

On the contrary, in the visual inspection apparatus according to the first embodiment of the present invention, the inspection picture has the shape in which the hollow portion of the labeling picture of the bump 30 is embedded. Thus, even if the pass or rejection of the inspection is judged based on the area, the normal bump and the abnormal bump can be distinguished. Hence, it is possible to improve the accuracy of the visual inspection of the BGA 20.

(Second Embodiment)

A visual inspection apparatus according to the second embodiment of the present invention is designed such that the pixels forming the outer circumference of the inspection picture are converted into subpixels, in the visual inspection apparatus according to the first embodiment. It should be noted that, in the following explanation, the symbols or numerals equal to those of the first embodiment are given to the portions equal to or corresponding to the portions of the first embodiment, and the different portions are centrally explained.

The configuration of a picture processing unit 12a of the visual inspection apparatus according to the second embodiment of the present invention is shown in a block diagram of FIG. 6. This visual inspection apparatus is designed such that a sub-pixel generating unit 126 is added to the configuration of the first embodiment. Also, functions of a labeling unit 122a and a judging unit 125a are altered from those of the labeling unit 122 and the judging unit 125 in the first embodiment, respectively.

The labeling unit 122a executes the labeling of the binary picture data from the binary conversion unit 121 to thereby generate the labeling picture, and sequentially stores coordinates of pixels forming an outer circumference of the labeling picture into the memory 120. It should be noted that the pixels forming the outer circumference of the labeling picture are equal to the pixels forming the outer circumference of the inspection picture. Therefore, they are collectively referred to as "outer circumference pixels".

The sub-pixel generating unit 126 generates the sub-pixels based on the coordinates of the outer circumference pixels stored in the memory 120 by the labeling unit 122a. The sub-pixels of one pixel can be generated, for example, by dividing vertical and horizontal components of the pixel into respective 10 components to thereby generate 100 sub-pixels.

The range of the pixels targeted for the sub-pixel generation can be defined as the outer circumference pixels and pixels in a predetermined range surrounding each of the outer circumference pixels, for example, the outer circumference pixels and 8 pixels surrounding each of the outer circumference pixels. In order to generate the sub-pixels, a known technique, for example, such as a three-dimensional curve complementation and the like may be used.

The judging unit 125a inspects the inspection picture sent from the sun-pixel generating unit 126, and judges the pass or rejection of the inspection of the BGA 20. The inspection is executed by calculating the area of the inspection picture and investigating whether or not the calculation result is within a predetermined range. The calculation of the area is executed by counting the total number of the sub-pisels and the pixels having the value "1" existed in the inspection picture. The judged result by the judging unit 125a is sent to, for example, the external display apparatus (not shown).

Figure 7:
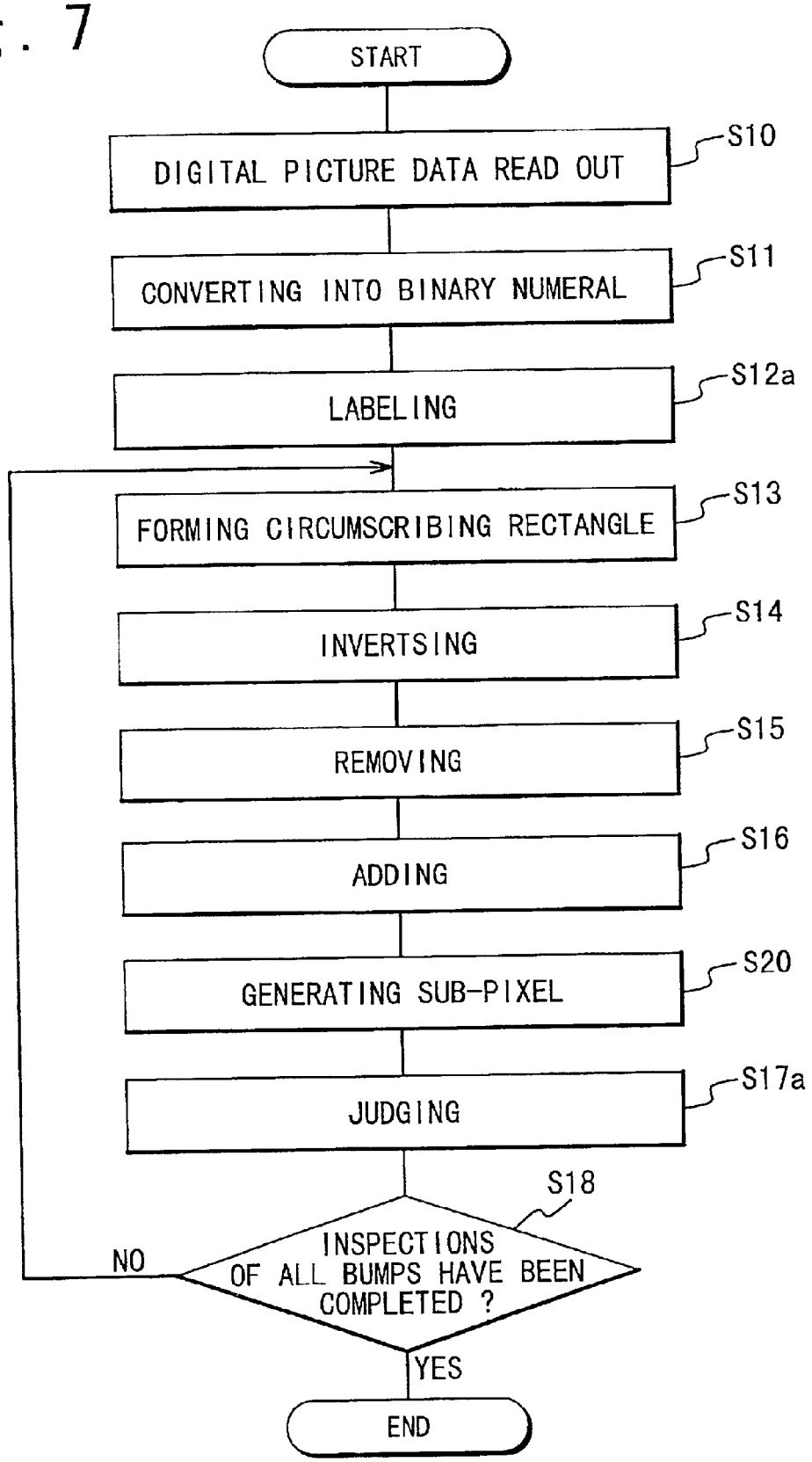
FIG. 7 is a flowchart showing an operation of the visual inspection apparatus according to the second embodiment of the present invention.

The operation of the visual inspection apparatus according to the second embodiment of the present invention to which the picture processing unit 12a having the above-mentioned configuration is applied will be described below with reference to the flowchart shown in FIG. 7.

At first, a photograph of the BGA 20 that is the inspection target sample is taken, and the obtained digital picture data is stored in the memory 120. Then, the digital picture data is read out from the memory 120 and converted into the binary numeral (Steps S10, S11). The above-mentioned operations are equal to those of the first embodiment. The binary picture data obtained by the binary conversion is sent to the labeling unit 122a.

The labeling unit 122a executes a labeling process to label the binary picture data (Step S12a). At this time, the labeling unit 122a sequentially stores the coordinates of the outer circumference pixels in a memory (not shown).

The formation of the circumscribing rectangle (Step S13), the inversion (Step S14), the removal (Step S15) and the addition (Step S16) are sequentially executed similarly to the first embodiment. Thus, the inspection picture shown in FIG. 4E is obtained.

Then, the generation of the sub-pixels is executed (Step S20). That is, the sub-pixel generating unit 126 generates the sub-pixels of the outer circumference pixels and the pixels in the predetermined range surrounding them, based on the coordinates of the outer circumference pixels stored in the memory 120 by the labeling unit 122a.

Then, the pass or rejection of the inspection of the bump 30 is judged (Step S17a). That is, at this step S17a, the pass or rejection is judged by calculating the area of the inspection picture and investigating whether or not the calculation result is within the predetermined range. The area is calculated by counting the total number of the pixels having the value "1" and the sub-pixels having the value "1" existed in the inspection picture. The judged result by the judging unit 125 is sent to, for example, the external display apparatus (not shown) and displayed thereon.

Next, it is investigated whether or not the inspections of all the bumps 30 have been completed (Step S18). If it is judged that the inspections have not been completed, the operational flow returns back to the step S13, and the above-mentioned processes are carried out, repeatedly. If it is judged at the step S18 that the inspections of all the bumps 30 have been completed, the visual inspection of one BGA 20 has completed.

As mentioned above, in the visual inspection apparatus according to the second embodiment of the present invention, the pixels forming the outer circumference of the inspection picture are converted into the sub-pixels. Then, area of the inspection picture having the outer circumference converted into the sub-pixels is calculated. Thus, the accuracy of the area of the inspection picture is improved over the first embodiment. Hence, it is possible to further improve the inspection accuracy of the BGA 20.

Also, the range for the conversion into the sub-pisels does not contain the entire inspection picture, but contains only the outer circumference. Thus, it is possible to shorten the time necessary for the conversion into the sub-pixels. The range for the generation into the sub-pixels may be also defined as the entire inspection picture. This case provides the merit that the process for converting the sub-pixels can be simplified.

(Third Embodiment)

A visual inspection apparatus according to the third embodiment of the present invention is designed such that the judgment of the pass or rejection of the inspection of the BGA is done based on a summation of shade values of original pictures.

Figure 8:
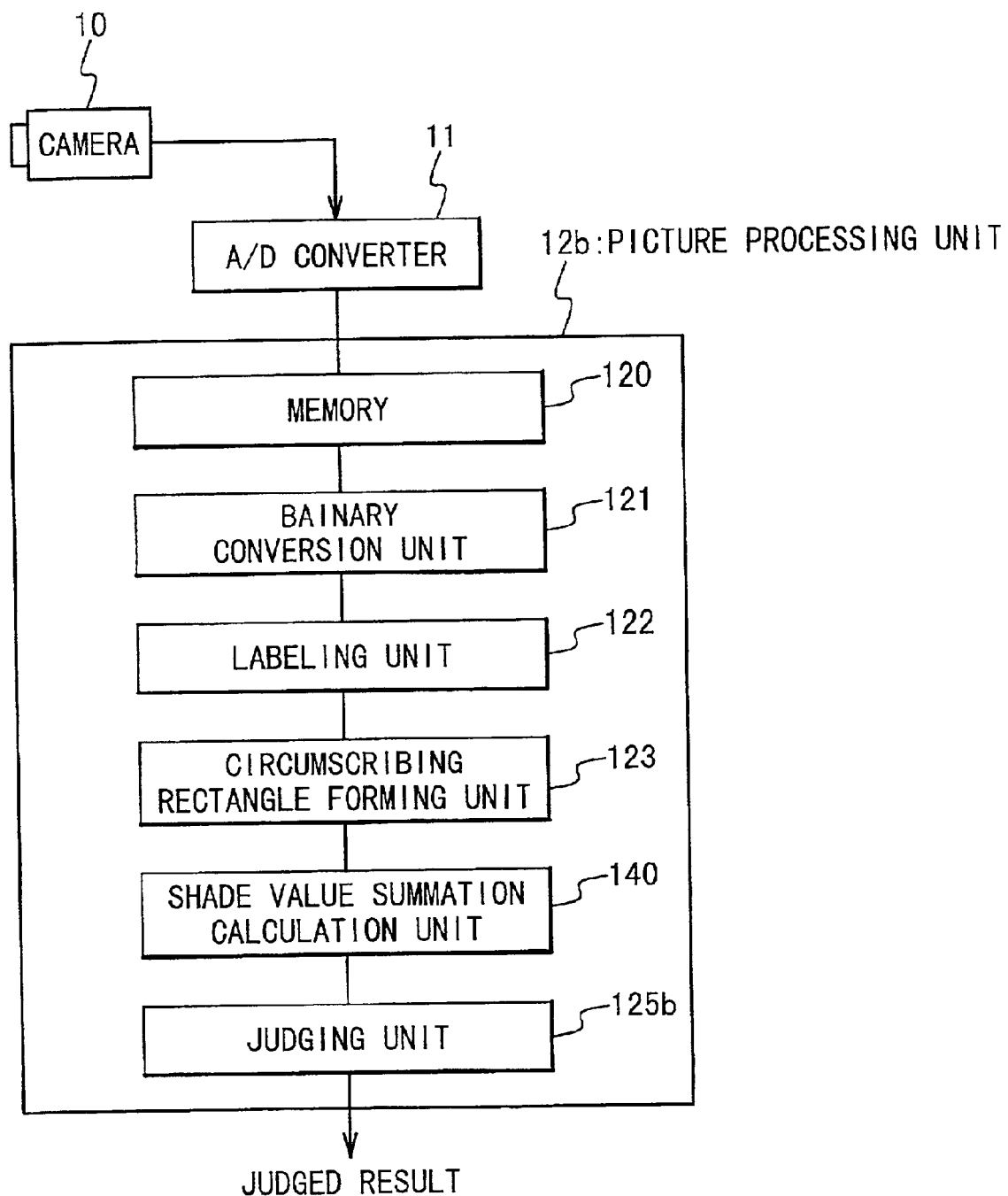
FIG. 8 is a block diagram showing a configuration of a picture processing unit applied to a visual inspection apparatus according to a third embodiment of the present invention.

The configuration of a picture processing unit 12b of the visual inspection apparatus according to the third embodiment of the present invention is shown in a block diagram of FIG. 8. In this visual inspection apparatus, a shade value summation calculation unit 140 is installed instead of the inspection picture generating unit 124 of the first embodiment. Also, a function of a judging unit 125b is different from that of the judging unit 125 of the first embodiment.

The shade value summation calculation unit 140 fetches from the memory 120 the digital picture data corresponding to the circumscribing rectangle defined by the circumscribing rectangle data from the circumscribing rectangle forming unit 123. Then, the shade value summation calculation unit 140 accumulates the shade values of all the pixels forming the digital picture data and thereby calculates a summation of the shade values. The summation of the shade values generated by the shade value summation calculation unit 140 is sent to the judging unit 125b.

The judging unit 125b carries out the inspection based on the summation of the shade values sent by the shade value summation calculation unit 140, and thereby judges the pass or rejection of the inspection of the BGA 20. The inspection is executed by investigating whether or not the summation of the shade values is within a predetermined range. The judged result by the judging unit 125b is sent to, for example, the external display apparatus (not shown).

Figure 9:
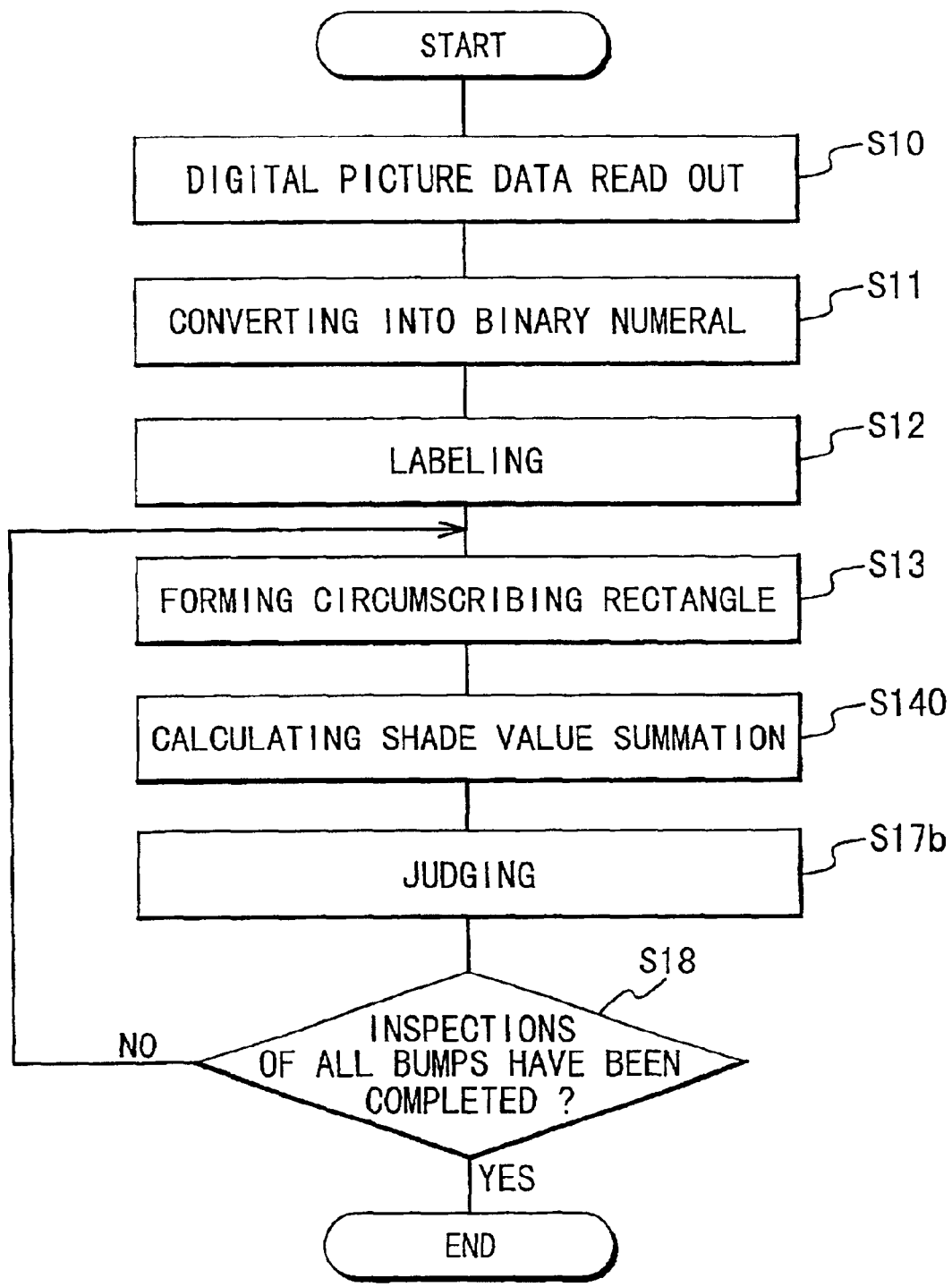
FIG. 9 is a flowchart showing an operation of the visual inspection apparatus according to the third embodiment of the present invention.

The operation of the visual inspection apparatus according to the third embodiment of the present invention to which the picture processing unit 12b having the above-mentioned configuration is applied will be described below with reference to the flowchart shown in FIG. 9.

At first, a photograph of the BGA 20 that is the inspection target sample is taken, and the obtained digital picture data is stored in the memory 120. Then, the digital picture data is read out from the memory 120, and converted into the binary numeral, and labeled. After that, the circumscribing rectangle is formed (Steps S10 to S13). The above-mentioned operations are equal to those of the first embodiment.

Then, the summation of the shade values is calculated (Step S140). That is, the shade value summation calculation unit 140 fetches from the memory 120 the digital picture data corresponding to the circumscribing rectangle defined by the circumscribing rectangle data from the circumscribing rectangle forming unit 123. Then, shade value summation calculation unit 140 accumulates the shade values of all the pixels forming the fetched digital picture data. Thus, the summation of the shade values of one bump 30 is calculated.

Then, the pass or rejection of the inspection of the bump 30 is judged (Step S17b). That is, at this step S17b, it is investigated whether or not the summation of the shade values obtained at the step S140 is within a predetermined range. If the summation is within the predetermined range, it is judged as the pass. On the other hand, if the summation is not within the predetermined range, it is judged as the rejection. The judged result by the judging unit 125b is sent to, for example, the external display apparatus (not shown) and displayed thereon.

Next, it is investigated whether or not the inspections of all the bumps 30 have been completed (Step S18). If it is judged that the inspections have not been completed, the operational flow returns back to the step S13, and the above-mentioned processes are carried out, repeatedly. If it is judged at the step S18 that the inspections of all the bumps 30 have been completed, the visual inspection of one BGA 20 has completed.

As mentioned above, in the visual inspection apparatus according to the third embodiment of the present invention, the pass or rejection of the inspection of the BGA 20 is judged based on the summation of the shade value of the original picture. Thus, it is possible to remove the quantized error caused by the binary conversion of the digital picture data, and also possible to improve the inspection accuracy of the BGA 20.

(Fourth Embodiment)

A visual inspection apparatus according to the fourth embodiment of the present invention is designed such that a summation of shade values is accumulated after the pixels forming the outer circumference of the inspection picture is converted into the sub-pisels, in the visual inspection apparatus according to the third embodiment. It should be noted that, in the following explanation, the symbols or numerals equal to those of the third embodiment are given to the portions equal to or corresponding to the portions of the third embodiment, and the different portions are centrally explained.

Figure 10:
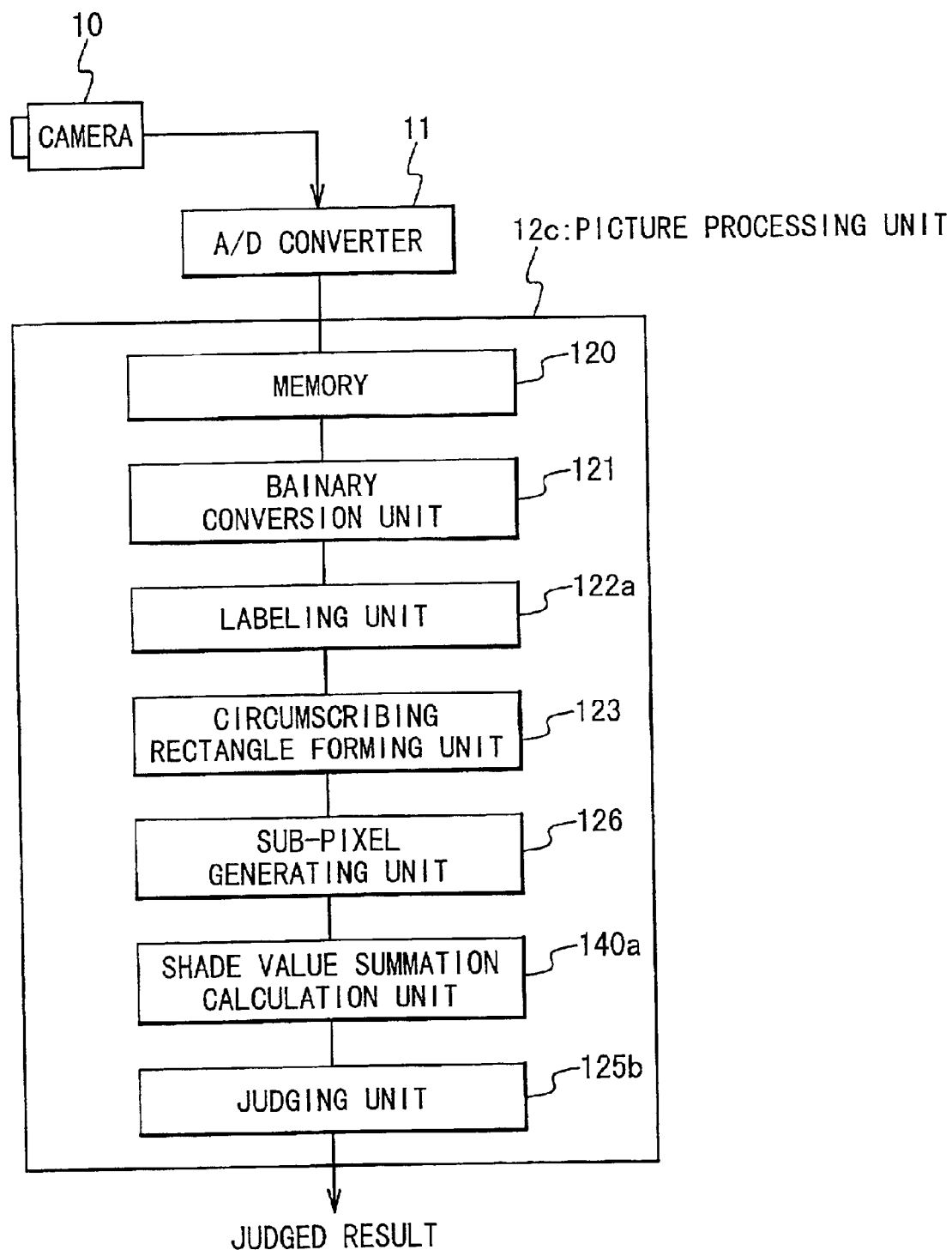
FIG. 10 is a block diagram showing a configuration of a picture processing unit applied to a visual inspection apparatus according to a fourth embodiment of the present invention.

The configuration of a picture processing unit 12c of the visual inspection apparatus according to the fourth embodiment of the present invention is shown in a block diagram of FIG. 10. This visual inspection apparatus is designed such that a sub-pixel generating unit 126 is added to the configuration of the third embodiment. Also, the labeling unit 122a used in the second embodiment is employed instead of the labeling unit 122 in the third embodiment. The function of the shade value summation calculation unit 140a is different from that of the shade value summation calculation unit 140 of the third embodiment.

The labeling unit 122a, when generating the labeling picture by labeling the binary picture data sent from the binary conversion unit 121, sequentially stores the coordinates of the pixels forming an outer circumference of the labeling picture into the memory 120.

The sub-pixel generating unit 126 generates the sub-pixels based on the coordinates of the outer circumference pixels stored in the memory 120 by the labeling unit 122a. The generation of the sub-pixels can be executed similarly to the second embodiment.

The shade value summation calculation unit 140a fetches from the memory 120 the digital picture data corresponding to the circumscribing rectangle defined by the circumscribing rectangle data from the circumscribing rectangle forming unit 123. Then, shade value summation calculation unit 140a accumulates the shade values of all the sub-pixels and the shade values of all the pixels forming the digital picture data, respectively to thereby calculate a summation of the shade values. The summation of the shade values calculated by the shade value summation calculation unit 140a is sent to the judging unit 125b.

Figure 11:
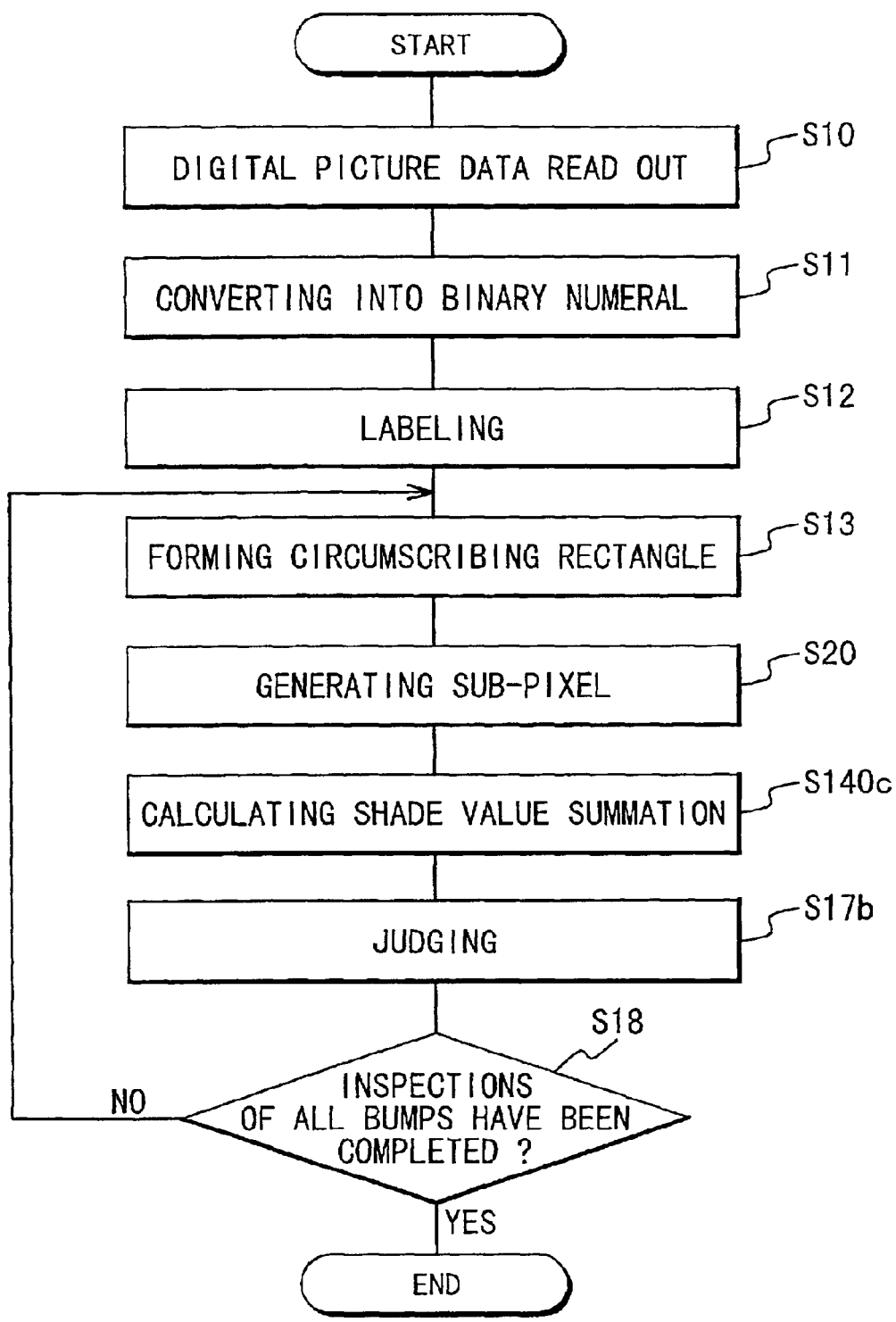
FIG. 11 is a flowchart showing an operation of the visual inspection apparatus according to the fourth embodiment of the present invention.

The operation of the visual inspection apparatus according to the fourth embodiment of the present invention to which the picture processing unit 12c having the above-mentioned configuration is applied will be described below with reference to the flowchart shown in FIG. 11.

At first, a photograph of the BGA 20 that is the inspection target sample is taken, and the obtained digital picture data is stored in the memory 120. Then, the digital picture data is read out from the memory 120, and converted into the binary numeral, and labeled. After that, the circumscribing rectangle is formed (Steps S10 to S13). The above-mentioned operations are equal to those of the first embodiment.

Then, the generation of the sub-pixels is executed (Step S20). That is, the sub-pixel generating unit 126 generates the sub-pixels of the outer circumference pixels and the pixels in the predetermined range surrounding them, based on the coordinates of the outer circumference pixels stored in the memory 120 by the labeling unit 122a.

Then, the summation of the shade values is calculated (Step S140c). That is, the shade value summation calculation unit 140a calculates the shade values of the original picture containing the portions converted into the sub-pixels, as mentioned above. Thus, the summation of the shade values corresponding to one bump 30 is calculated.

Then, the pass or rejection of the inspection of the bump 30 is judged (Step S17b). That is, at this step S17b, it is investigated whether or not the summation of the shade values obtained at the step S140c is within the predetermined range. If the summation is within the predetermined range, it is judged as the pass. If the summation is not within the predetermined range, it is judged as the rejection. The judged result is sent to, for example, the external display apparatus (not shown) and displayed thereon.

Next, it is investigated whether or not the inspections of all the bumps 30 have been completed (Step S18). If it is judged that the inspections have not been completed, the operational flow returns back to the step S13, and the above-mentioned processes are carried out, repeatedly. If it is judged at the step S18 that the inspections of all the bumps 30 have been completed, the visual inspection of one BGA 20 has completed.

As mentioned above, in the visual inspection apparatus according to the fourth embodiment, the outer circumference of the original picture is converted into the sub-pixels. After that, the pass or rejection of the inspection of the BGA is judged based on the shade value of the original picture converted into the sub-pixels. Thus, the inspection accuracy of the BGA 20 can be improved over the visual inspection apparatus according to the third embodiment.

(Fifth Embodiment)

A visual inspection apparatus according to the fifth embodiment of the present invention is designed such that the pass or rejection of the inspection of the BGA is judged based on an average of the shade values of the original picture.

Figure 12:
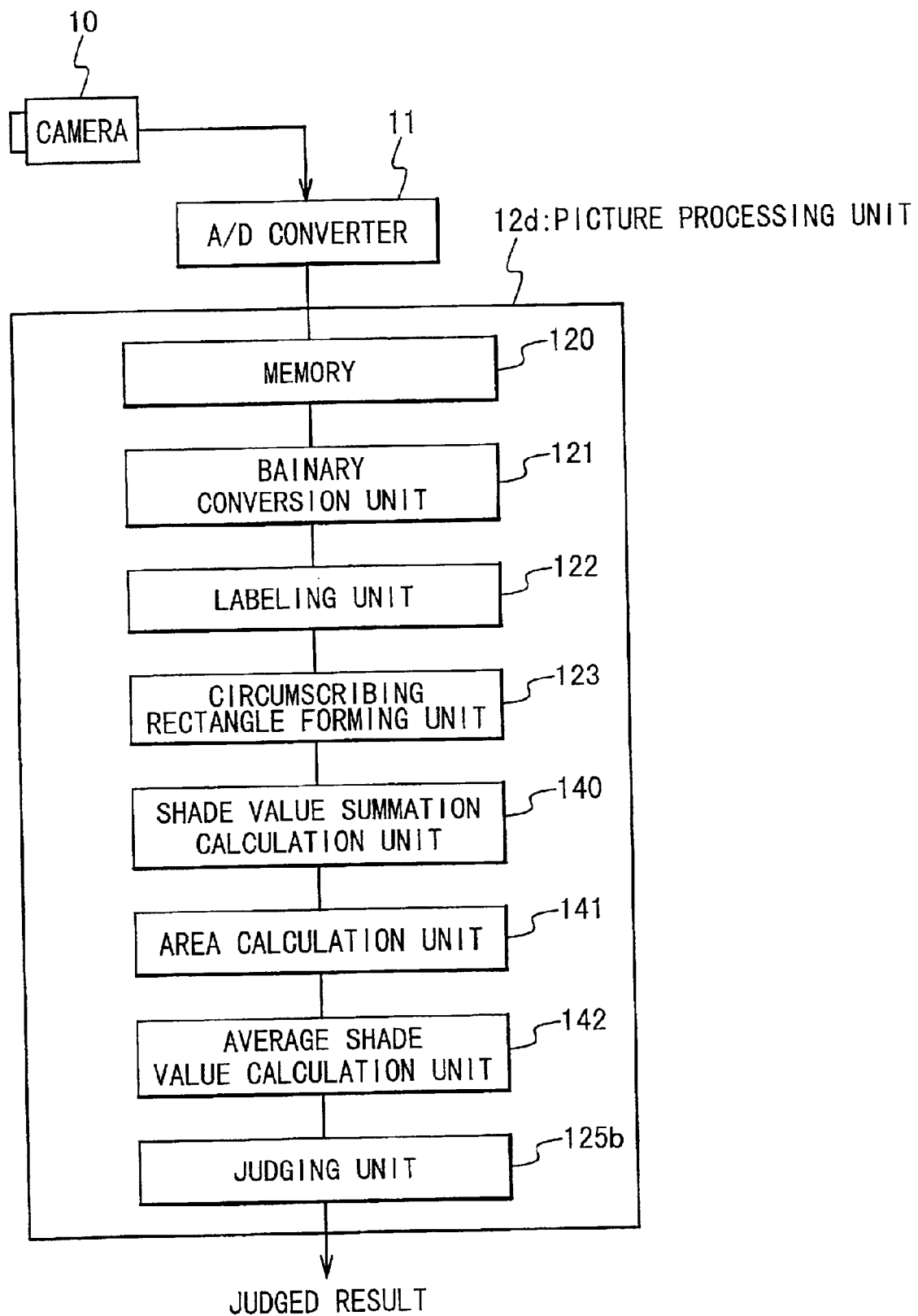
FIG. 12 is a block diagram showing a configuration of a picture processing unit applied to a visual inspection apparatus according to a fifth embodiment of the present invention.

The configuration of a picture processing unit 12d of the visual inspection apparatus according to the fifth embodiment of the present invention is shown in a block diagram of FIG. 12. This visual inspection apparatus is designed such that an area calculation unit 141 and an average shade value calculation unit 142 are added to the configuration of the third embodiment.

The area calculation unit 141 calculates the area of the labeling picture. This area calculation is executed by counting the number of the pixels having the value "1" in the labeling picture. The area calculated by the area calculation unit 141 is sent to the average shade value calculation unit 142.

The average shade value calculation unit 142 divides the summation of the shade values calculated by the shade value summation calculation unit 140 by the area calculated by the area calculation unit 141, and calculates the average shade value. This average shade value calculated by the average shade value calculation unit 142 is sent to the judging unit 125b.

Figure 13:
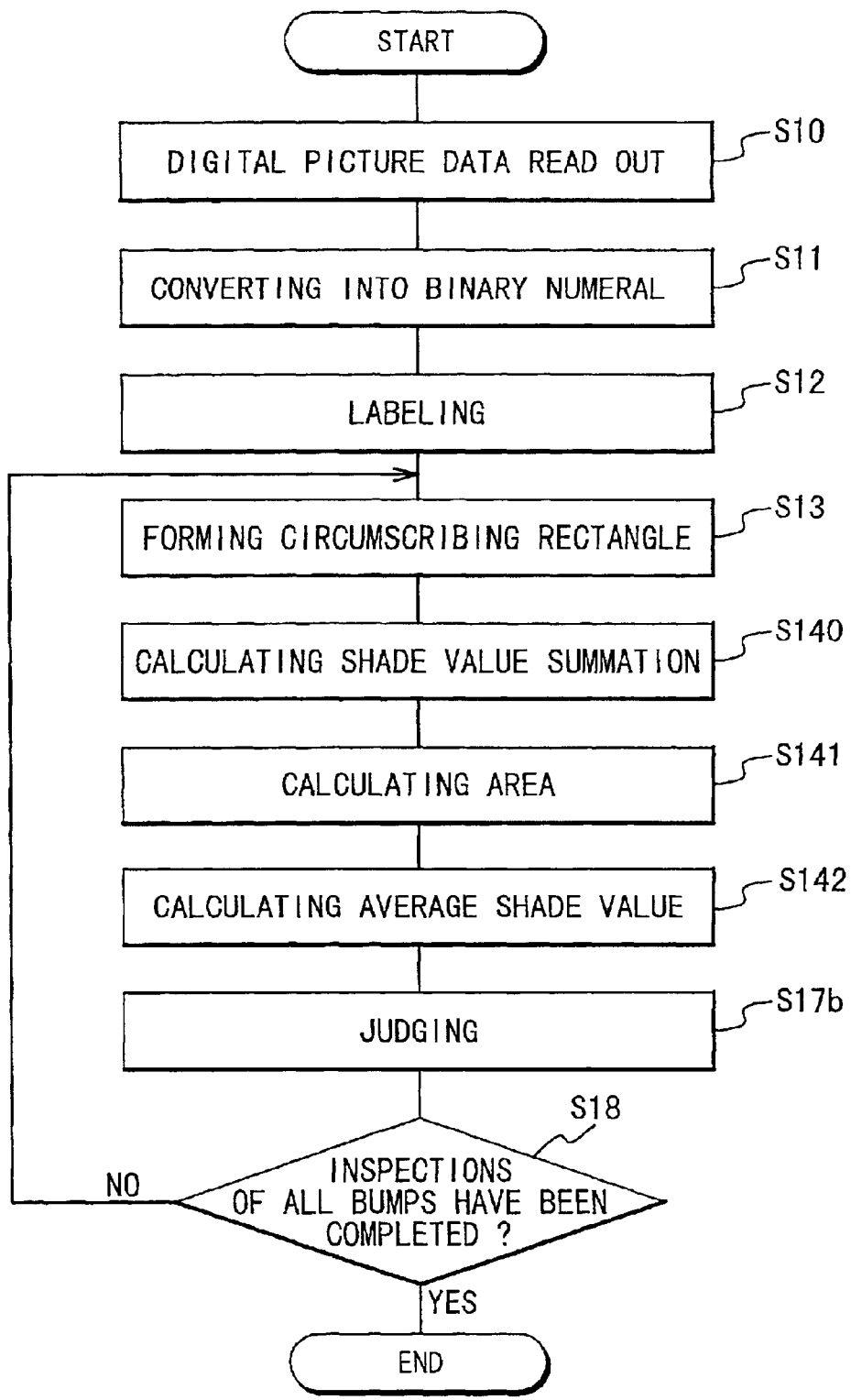
FIG. 13 is a flowchart showing an operation of the visual inspection apparatus according to the fifth embodiment of the present invention.

The operation of the visual inspection apparatus according to the fifth embodiment of the present invention to which the picture processing unit 12d having the above-mentioned configuration is applied will be described below with reference to the flowchart shown in FIG. 13.

At first, a photograph of the BGA 20 that is the inspection target sample is taken, and the obtained digital picture data is stored in the memory 120. Then, the digital picture data is read out from the memory 120, and converted into the binary numeral, and labeled. After that, the circumscribing rectangle is formed (Steps S10 to S13). The above-mentioned operations are equal to those of the first embodiment.

Then, the summation of the shade values is calculated (Step S140). That is, the shade value summation calculation unit 140 fetches from the memory 120 the digital picture data corresponding to the circumscribing rectangle defined by the circumscribing rectangle data from the circumscribing rectangle forming unit 123. Then, shade value summation calculation unit 140 accumulates the shade values of all the pixels forming the fetched digital picture data. Thus, the summation of the shade values of one bump 30 is calculated.

Then, the area calculation is performed (Step S141). That is, the area calculation unit 141 calculates the area of the labeling picture by using the above-mentioned method. Then, the average shade value is calculated (Step S142). That is, the summation of the shade values calculated at the step S140 is divided by the area calculated at the step S141.

Then, the pass or rejection of the inspection of the bump 30 is judged (Step S17b). That is, it is investigated whether or not the average shade value obtained at the step S142 is within a predetermined range. If the average shade value is within the predetermined range, it is judged as the pass. On the other hand, if the average shade value is not within the predetermined range, it is judged as the rejection. The judged result by the judging unit 125b is sent to, for example, the external display apparatus (not shown) and displayed thereon.

Next, it is investigated whether or not the inspections of all the bumps 30 have been completed (Step S18). If it is judged that the inspections have not been completed, the operational flow returns back to the step S13, and the above-mentioned processes are carried out, repeatedly. If it is judged at the step S18 that the inspections of all the bumps 30 have been completed, the visual inspection of one BGA 20 has completed.

As mentioned above, in the visual inspection apparatus according to the fifth embodiment of the present invention, the pass or rejection of the inspection of the BGA 20 is judged based on the average of the shade values of the original picture. Thus, it is possible to remove the quantized error caused by the binary conversion of the digital picture data, and also possible to improve the inspection accuracy of the BGA 20.

It should be noted that, similarly to the fourth embodiment, this fifth embodiment can be also configured such that the outer circumference of the labeling picture is converted into the sub-pixel to then calculate the summation of the shade values and the area. This configuration can further improve the inspection accuracy of the BGA 20.

(Sixth Embodiment)

A visual inspection apparatus according to the sixth embodiment of the present invention is designed such that the pass or rejection of the inspection of the BGA is judged based on the summation of the average shade values of the original picture (hereafter, referred to as "total average shade value".

Figure 14:
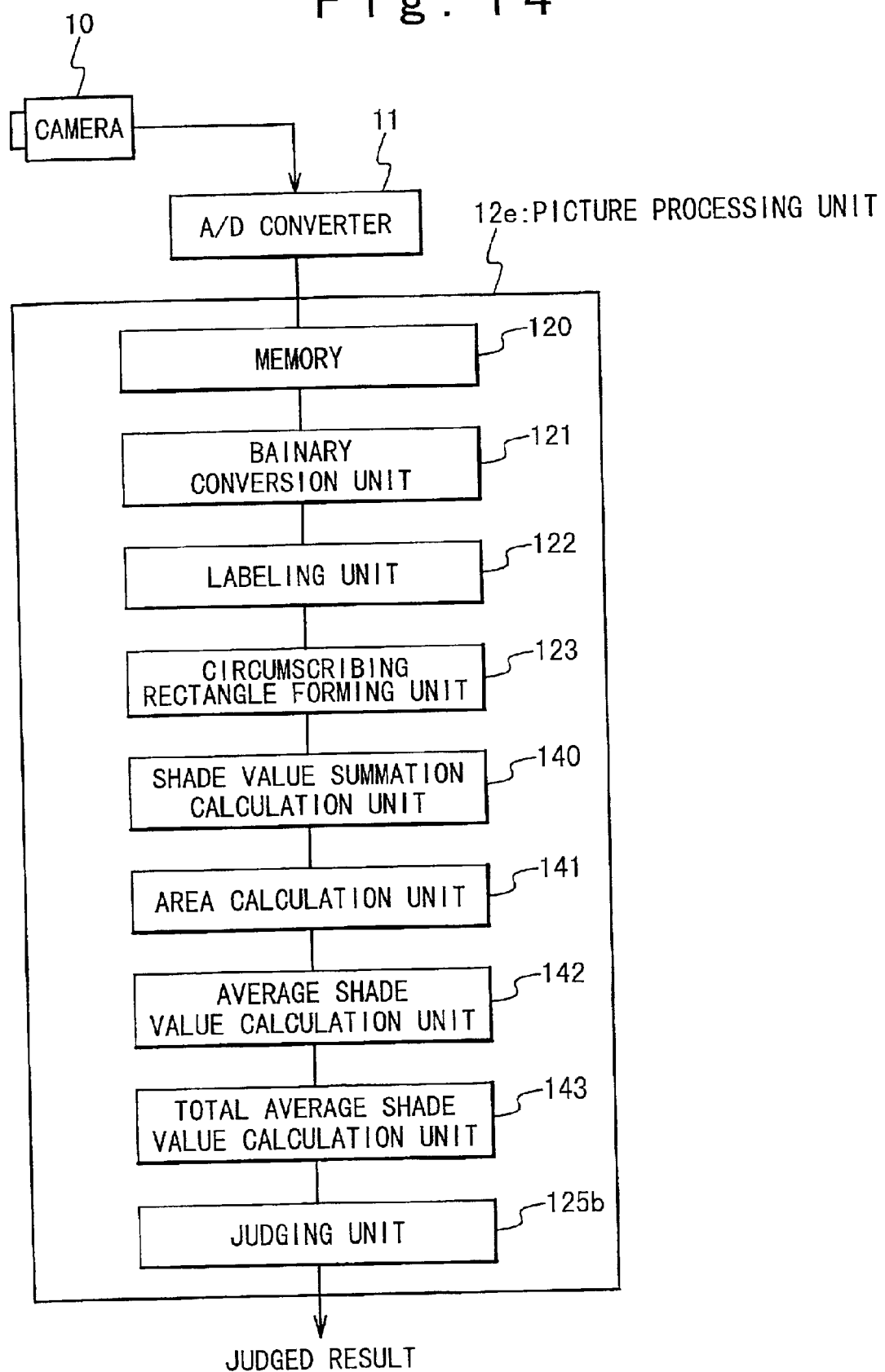
FIG. 14 is a block diagram showing a configuration of a picture processing unit applied to a visual inspection apparatus according to a sixth embodiment of the present invention.

The configuration of a picture processing unit 12e of the visual inspection apparatus according to the sixth embodiment of the present invention is shown in a block diagram of FIG. 14. This visual inspection apparatus is designed such that a total average shade value calculation unit 143 is added to the configuration of the fifth embodiment.

The total average shade value calculation unit 143 calculates the average shade value of each of all the bumps of the BGA 20. This is determined by adding the average shade values of the respective bumps calculated by the average shade value calculation unit 142, and then dividing the added result by the number of the bumps 30 in the BGA 20.

Figure 15:
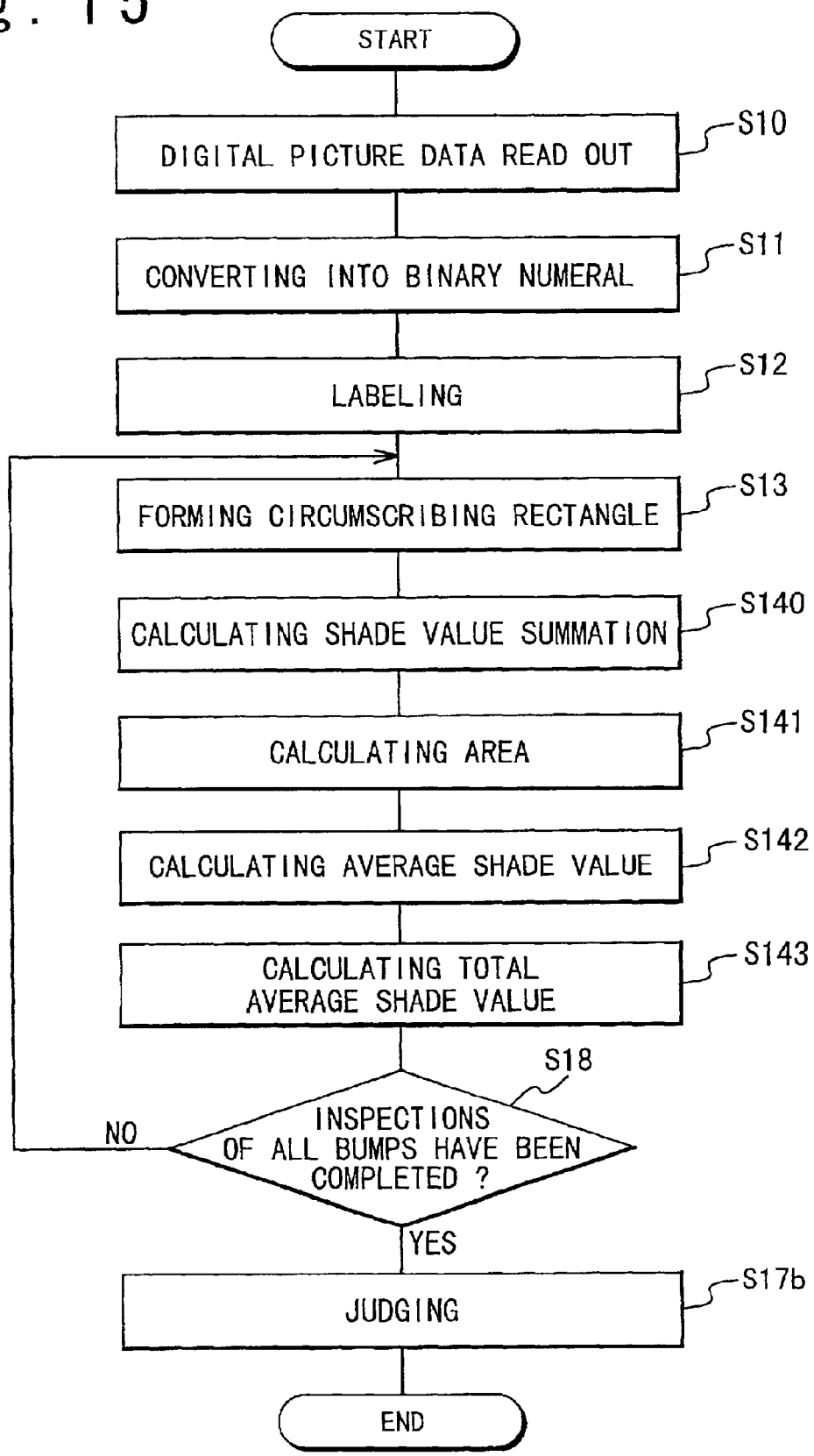
FIG. 15 is a flowchart showing an operation of the visual inspection apparatus according to the sixth embodiment of the present invention.

The operation of the visual inspection apparatus according to the sixth embodiment of the present invention to which the picture processing unit 12e having the above-mentioned configuration is applied will be described below with reference to the flowchart shown in FIG. 15.

At first, a photograph of the BGA 20 that is the inspection target sample is taken, and the obtained digital picture data is stored in the memory 120. Then, the digital picture data is read out from the memory 120, and converted into the binary numeral, and labeled. After that, the circumscribing rectangle is formed (Steps S10 to S13). The above-mentioned operations are equal to those of the first embodiment.

Next, similarly to the fifth embodiment, the summation of the shade values is calculated (Step S140), the area is calculated (Step S141) and the average shade value is calculated (Step S142), sequentially. Then, the total average shade value is calculated (Step S143). This calculation of the total average shade value is executed by adding the average shade value calculated at the step S142 to the total average shade value stored in the memory 120 in a previous calculation, and then halving the adding result.

Then, it is investigated whether or not the inspections of all the bumps 30 have been completed (Step S18). If it is judged that the inspections have not been completed, the operational flow returns back to the step S13, and the above-mentioned processes are carried out, repeatedly. If it is judged at the step S18 that the inspections of all the bumps 30 have been completed, the pass or rejection of the visual inspection of the BGA 20 is judged (Step S17b).

That is, when the inspections of all the bumps 30 have been completed, the total average shade value with regard to all the bumps is stored in the memory 120. Thus, the judging unit 125b investigates whether or not the total average shade value in the memory 120 is within the predetermined range. If the value is within the predetermined range, it is judged as the pass, and if the value is not within the predetermined range, it is judged as the rejection. The judged result by the judging unit 125b is sent to, for example, the external display apparatus (not shown) and displayed thereon. By above processing, the inspection of the one BGA 20 is completed.

As mentioned above, in the visual inspection apparatus according to the sixth embodiment of the present invention, the pass or rejection of the inspection of the BGA 20 is judged based on the average of the shade values of the original picture. Thus, it is possible to remove the quantized error caused by the binary conversion of the digital picture data, and also possible to improve the inspection accuracy of the BGA 20.

It should be noted that the judgment in the judging unit 125b can be designed such that the pass or rejection of the inspection of the BGA 20 is judged based on a difference between the average shade value calculated by the average shade value calculation unit 142 and the total average shade value calculated by the total average shade value calculation unit 143, or a rate of the average shade value calculated by the average shade value calculation unit 142 to the total average shade value calculated by the total average shade value calculation unit 143.

In the sixth embodiment, the total average shade value is determined by calculating the average shade values of all the bumps 30 and further averaging the calculated average shade values. However, it may be determined by calculating the total shade values of all the bumps 30 and then dividing the calculated total shade values by the areas of all the bumps 30. This configuration does not require the calculation of the average shade value of each bump 30. Thus, it is possible to attain the higher speed of the process.

Also, this sixth embodiment can be configured such that, similarly to the fourth embodiment, the outer circumference of the labeling picture is converted into the sub-pixel to then calculate the summation of the shade values and calculate the area. This configuration can further improve the inspection accuracy of the BGA 20.

(Seventh Embodiment)

A visual inspection apparatus according to the seventh embodiment of the present invention is designed such that the pass or rejection of BGA is judged based on a distance between the outer circumference pixels.

Figure 16:
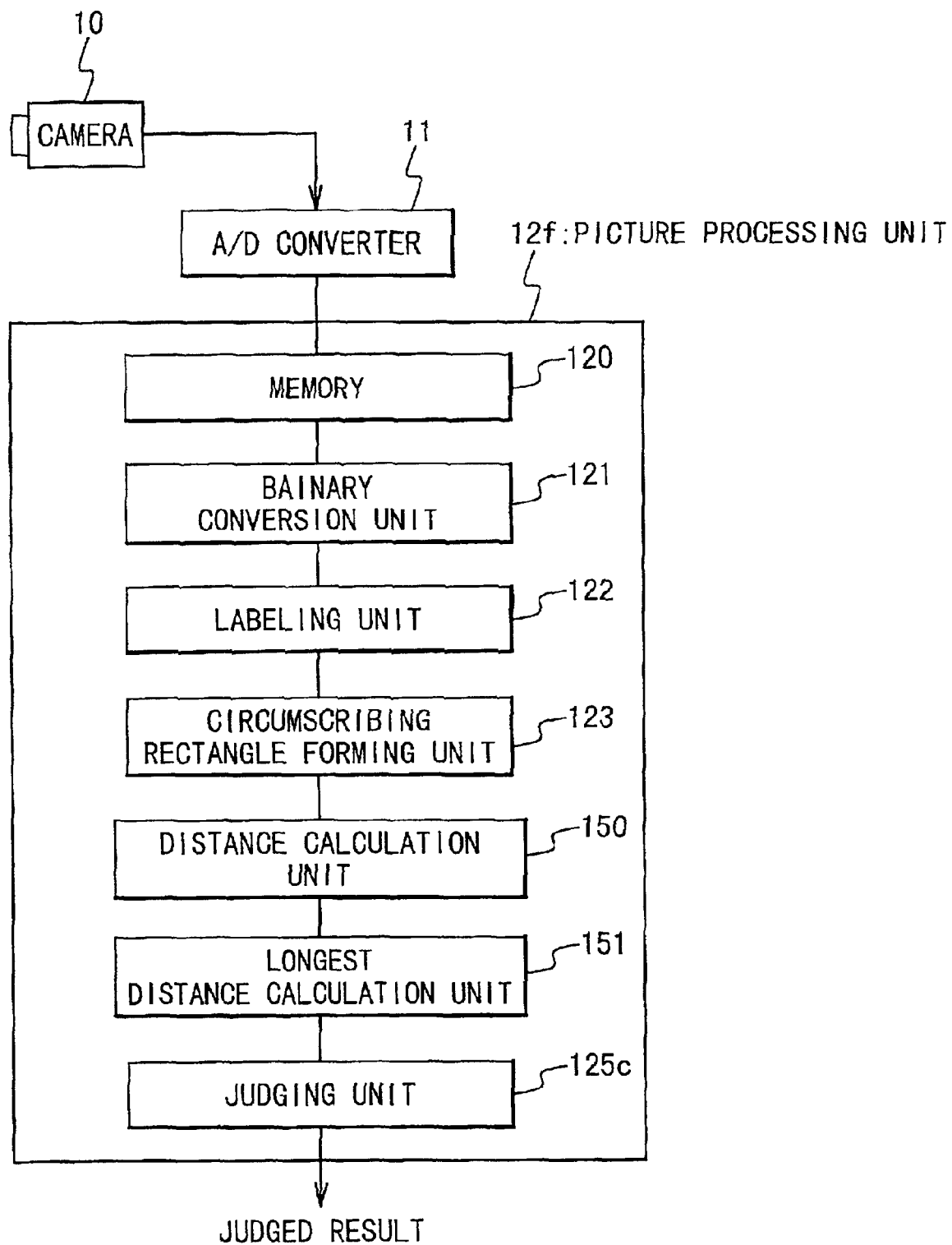
FIG. 16 is a block diagram showing a configuration of a picture processing unit applied to a visual inspection apparatus according to a seventh embodiment of the present invention.

The configuration of a picture processing unit 12f of the visual inspection apparatus according to the seventh embodiment of the present invention is shown in a block diagram of FIG. 16. This visual inspection apparatus is designed such that a distance calculation unit 150 and a longest distance calculation unit 151 are installed instead of the inspection picture generating unit 124 in the first embodiment. Also, the function of the judging unit 125c is altered from that of the first embodiment.

The distance calculation unit 150 calculates a distance between two outer circumference pixels, with regard to all combinations of two outer circumference pixels in a plurality of outer circumference pixels. The plurality of distances calculated by the distance calculation unit 150 are sent to the longest distance calculation unit 151.

The longest distance calculation unit 151 determines a longest distance from the distances calculated by the distance calculation unit 150, and sends the determined longest distance to the judging unit 125c.

The judging unit 125c judges the pass or rejection of the inspection of the BGA 20, depending on whether or not the longest distance sent from the longest distance calculation unit 151 is within a predetermined range. The judged result by the judging unit 125c is sent to, for example, the external display apparatus (not shown) and displayed thereon.

Figure 17:
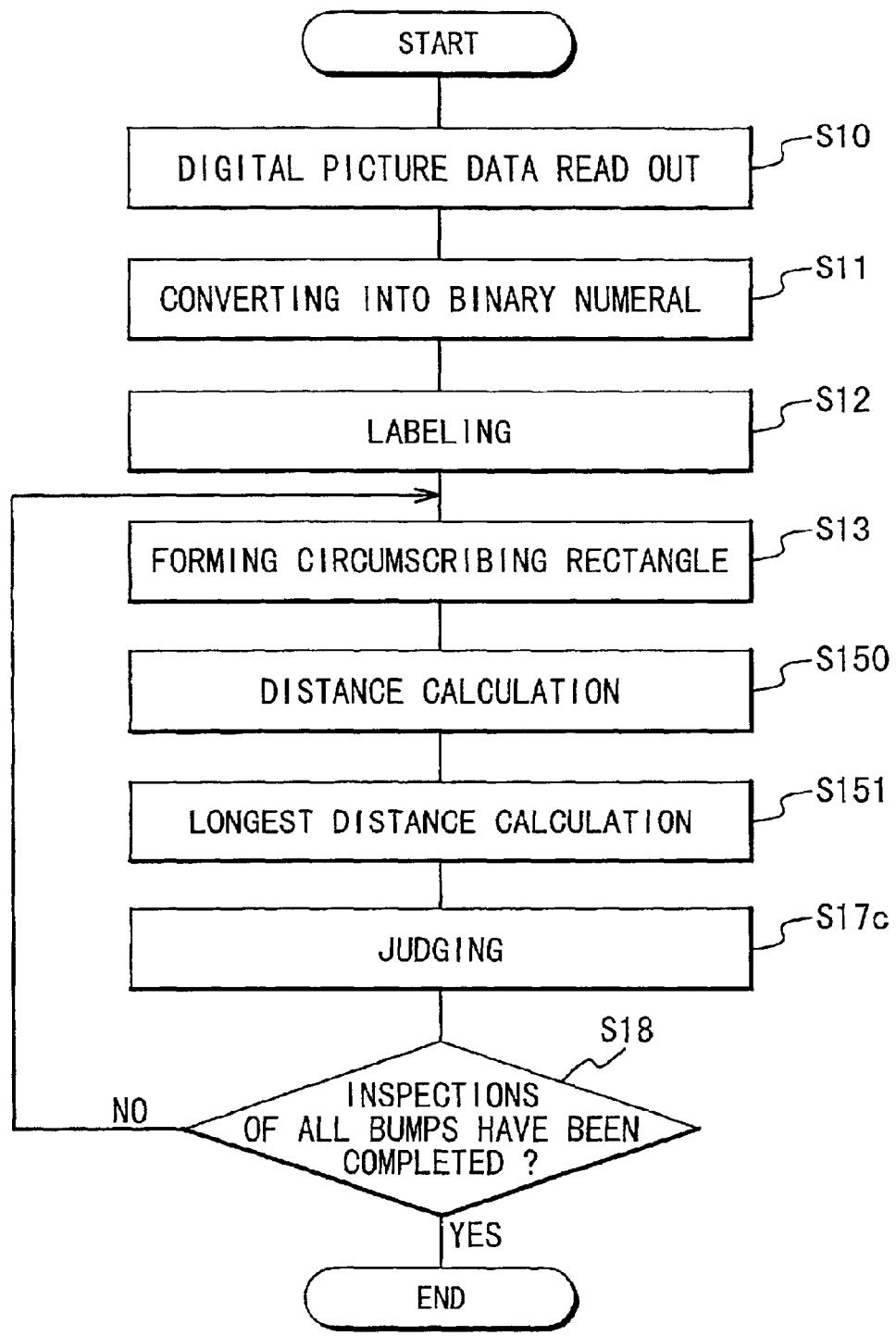
FIG. 17 is a flowchart showing an operation of the visual inspection apparatus according to the seventh embodiment of the present invention.

The operation of the visual inspection apparatus according to the seventh embodiment of the present invention to which the picture processing unit 12*f* having the above-mentioned configuration is applied will be described below with reference to the flowchart shown in FIG. 17.

At first, a photograph of the BGA 20 that is the inspection target sample is taken, and the obtained digital picture data is stored in the memory 120. Then, the digital picture data is read out from the memory 120, and converted into the binary numeral, and labeled. After that, the circumscribing rectangle is formed (Steps S10 to S13). The above-mentioned operations are equal to those of the first embodiment.

Next, the distance is calculated (Step S150). That is, the distance calculation unit 150 calculates the distance between the two outer circumference pixels, with regard to all the combinations of the two pixels in the plurality of outer circumference pixels, as mentioned above.

Then, the longest distance is calculated (Step S151). That is, the longest distance calculation unit 151 determines the longest distance from the plurality of distances calculated at the step S151.

Then, the pass or rejection of the inspection of the bump 30 is judged (Step S17*c*). That is, it is investigated whether or not the longest distance obtained at the step S151 is within a predetermined range. If the longest distance is within the predetermined range, it is judged as the pass, and if the longest distance is not within the predetermined range, it is judged as the rejection. The judged result is sent to, for example, the external display apparatus (not shown) and displayed thereon.

Next, it is investigated whether or not the inspections of all the bumps 30 have been completed (Step S18). If it is judged that the inspections have not been completed, the operational flow returns back to the step S13, and the above-mentioned processes are carried out, repeatedly. If it is judged at the step S18 that the inspections of all the bumps 30 have been completed, the visual inspection of one BGA 20 is completed.

As mentioned above, in the visual inspection apparatus according to the seventh embodiment of the present invention, the pass or rejection of the inspection of the BGA is judged based on the distance between the outer circumference pixels. Thus, the abnormality of the outer shape of the bump 30, which can not be judged from the area of the picture of the bump, can be removed to thereby improve the inspection accuracy of the BGA 20.

(Eighth Embodiment)

A visual inspection apparatus according to the eighth embodiment of the present invention is designed such that the pixels forming the outer circumference of the labeling picture are converted into sub-pixels, in the visual inspection apparatus according to the seventh embodiment.

Figure 18:
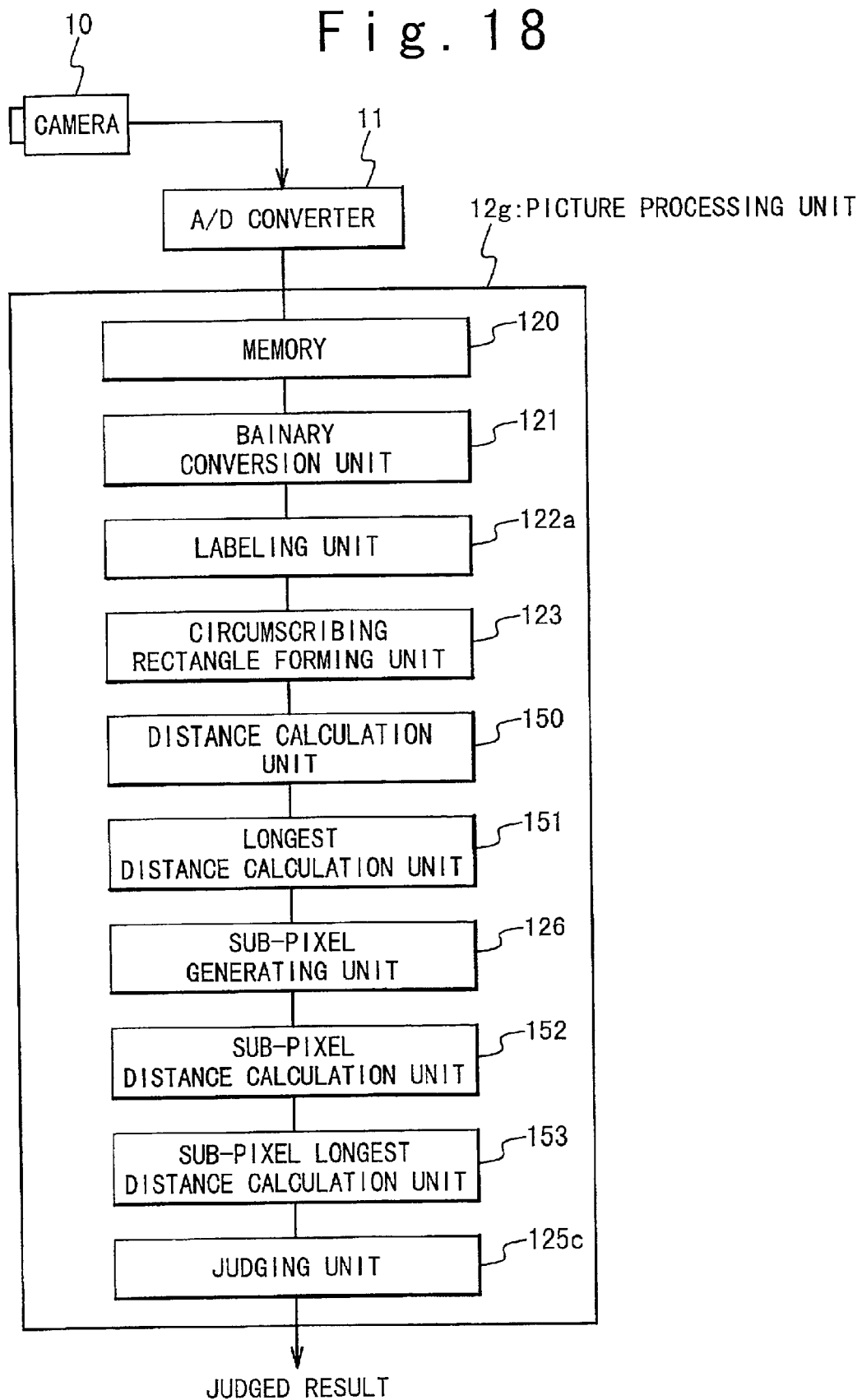
FIG. 18 is a block diagram showing a configuration of a picture processing unit applied to a visual inspection apparatus according to an eighth embodiment of the present invention.

The configuration of a picture processing unit 12*g* of the visual inspection apparatus according to the eighth embodiment of the present invention is shown in a block diagram of FIG. 18. This visual inspection apparatus is designed such that a sub-pixel generating unit 126, a sub-pixel distance calculation unit 152 and a sub-pixel longest distance calculation unit 153 are added to the configuration of the seventh embodiment. Also, the labeling unit 122*a* is identical to that of the second embodiment.

The sub-pixel generating unit 126 converts one set of outer circumference pixels having the longest distance (hereafter referred to as "a first pixel and a second pixel") into sub-pixels, and generates a first sub-pixel picture and a second sub-pixel picture, respectively. The generation of the sub-pixels is executed similarly to that of the second embodiment.

The sub-pixel distance calculation unit 152 calculates the distance between the two sub-pixels, with regard to all combinations of the plurality of sub-pixels forming the outer circumference of the first sub-pixel picture and the plurality of sub-pisels forming the outer circumference of the second sub-pixel picture. The plurality of distances calculated by the sub-pixel distance calculation unit 152 are sent to the sub-pixel longest distance calculation unit 153.

The sub-pixel longest distance calculation unit 153 determines a longest distance from the distances calculated by the sub-pixel distance calculation unit 152 and sends it to the judging unit 125*b*.

Figure 19:
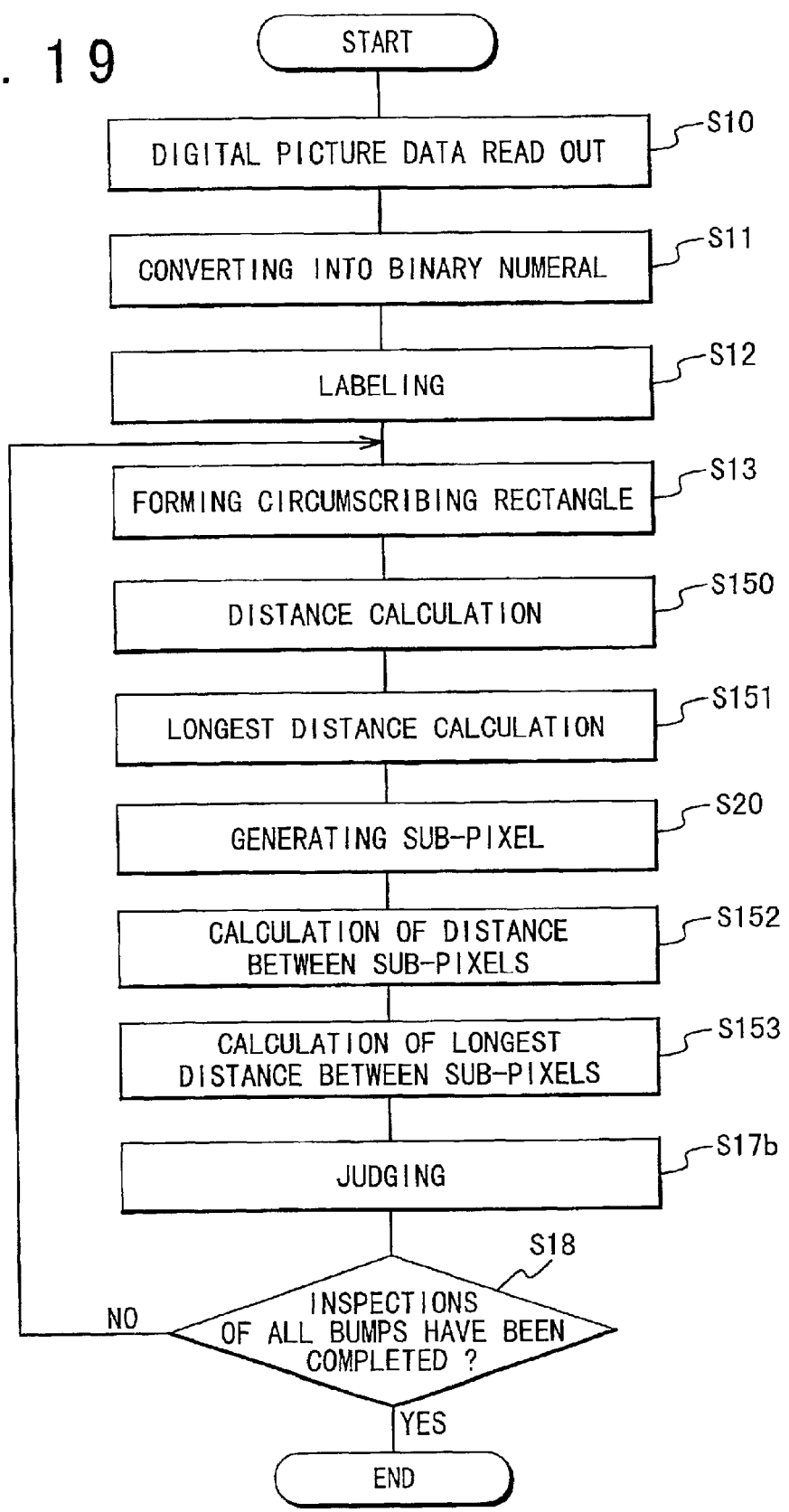
FIG. 19 is a flowchart showing an operation of the visual inspection apparatus according to the eighth embodiment of the present invention.

The operation of the visual inspection apparatus according to the eighth embodiment of the present invention to which the picture processing unit 12*g* having the above-mentioned configuration is applied will be described below with reference to the flowchart shown in FIG. 19 and the explanatory diagram shown in FIG. 20.

At first, a photograph of the BGA 20 that is the inspection target sample is taken, and the obtained digital picture data is stored in the memory 120. Then, the digital picture data is read out from the memory 120, and converted into the binary numeral, and labeled. After that, the circumscribing rectangle is formed (Steps S10 to S13). The above-mentioned operations are equal to those of the first embodiment.

Figure 20A:
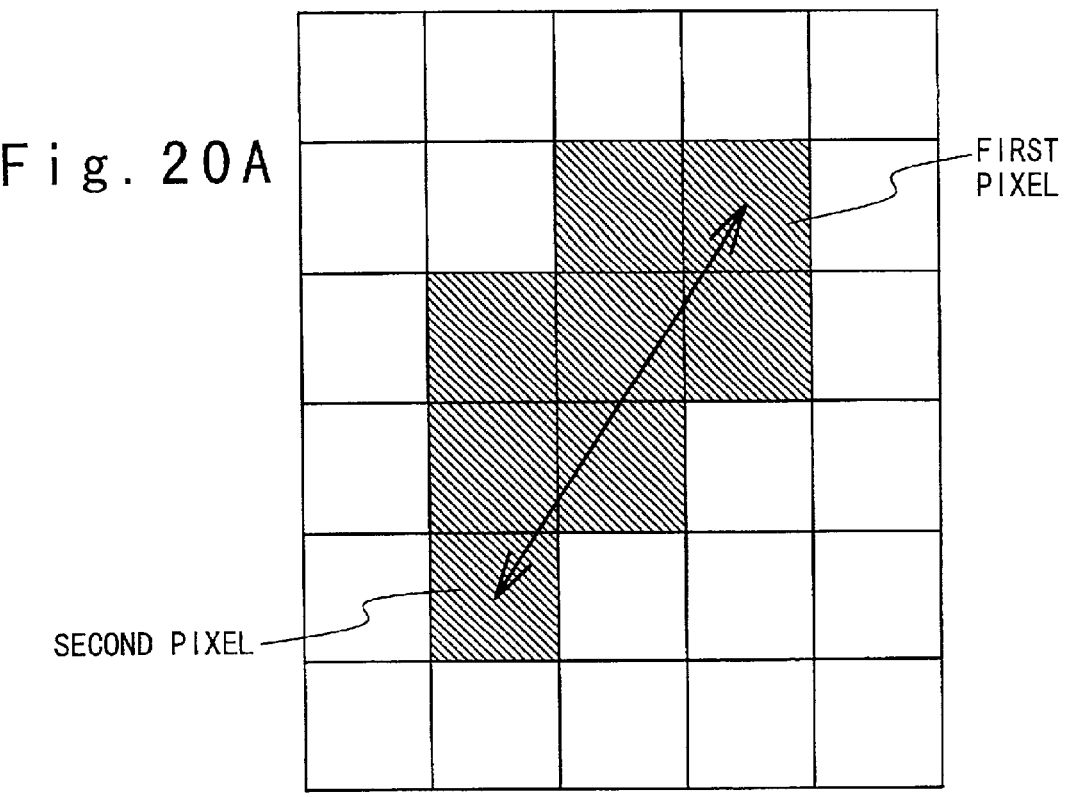
FIGS. 20A and 20B are explanatory diagrams describing an operation of the visual inspection apparatus according to the eighth embodiment of the present invention.

Similarly to the seventh embodiment, the distance is calculated (Step S150), and the longest distance is calculated (Step S151). Thus, the first pixels and the second pixels forming the longest distance are determined as shown in FIG. 20A.

Figure 20B:
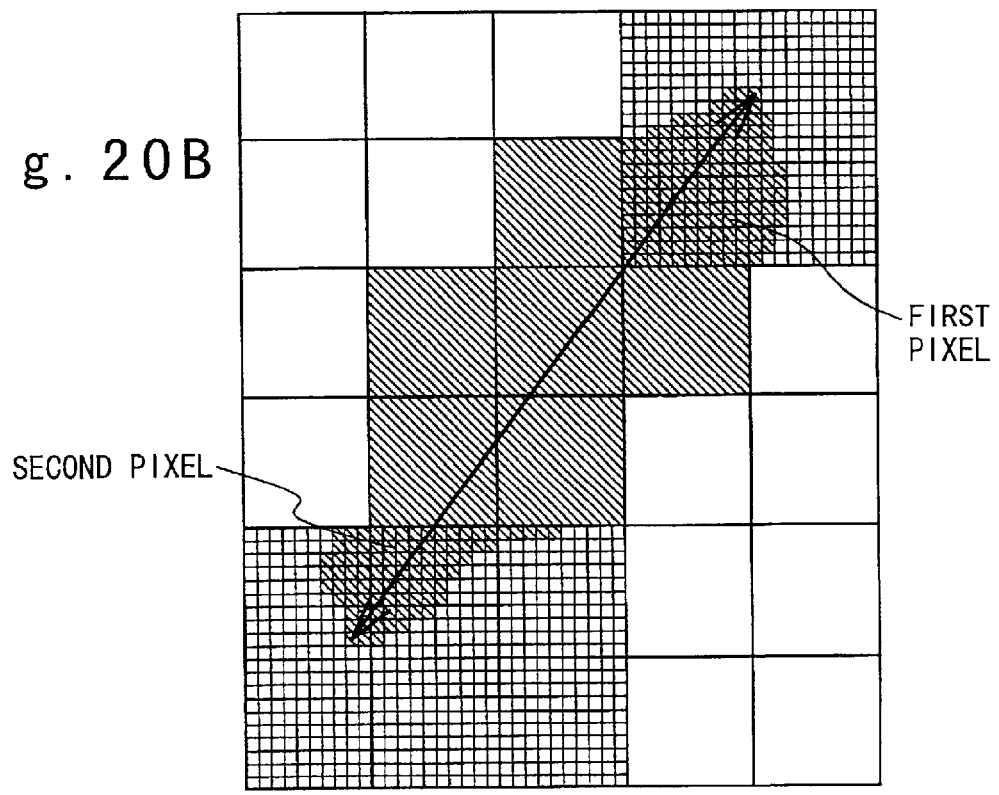

Then, the generation of the sub-pixel is executed (Step S20). The generation of the sub-pixel is performed on the circumferences of the first pixels and the second pixels forming the longest distance calculated at the step S151 as shown in FIG. 20B.

Then, the distance between the sub-pixels is calculated (Step S152). That is, the sub-pixel distance calculation unit 152 calculates the distance between the two sub-pixels, with regard to all the combinations of the plurality of sub-pixels forming the outer circumference of the first sub-pixel picture and the plurality of sub-pixels forming the outer circumference of the second sub-pixel picture.

Thereafter, the longest distance between the sub-pixels is calculated (Step S153). That is, the sub-pixel longest distance calculation unit 153 determines the longest distance from the distances calculated by the sub-pixel distance calculation unit 152.

Then, the pass or rejection of the bump 30 is judged (Step S17*b*). That is, it is investigated whether or not the longest distance between the sub-pisels obtained at the step S153 is within a predetermined range. If the longest distance is within the predetermined range, it is judged as the pass, and if the longest distance is not within the predetermined range, it is judged as the rejection. The judged result by the judging unit 125*c* is sent to, for example, the exterior display apparatus (not shown) and displayed thereon.

Next, it is investigated whether or not the inspections of all the bumps 30 have been completed (Step S18). If it is judged that the inspections have not been completed, the operational flow returns back to the step S13, and the above-mentioned processes are carried out, repeatedly. If it is judged at the step S18 that the inspections of all the bumps 30 have been completed, the visual inspection of one BGA 20 is completed.

As mentioned above, in the visual inspection apparatus according to the eighth embodiment of the present invention, the pass or rejection of the inspection of the BGA is judged based on the distance between the sub-pixels forming the outer circumference of the labeling picture. Thus, the accuracy of the distance is improved over the seventh embodiment. As a result, the abnormality of the outer shape of the bump can be detected at a high accuracy, which can improve the inspection accuracy of the BGA 20.

Also, only the circumferences of the two pixels forming the longest distance are converted into the sub-pixels. Thus, it is possible to shorten the time necessary for the conversion into the sub-pixels. It should be noted that the range for the conversion into the sub-pixels is not limited to the circumferences of the first and second pixels. The conversion into the sub-pixels can be performed as the entire inspection picture. In this case, the process for the conversion into the sub-pixels is simplified.

This visual inspection apparatus according to the eighth embodiment can be varied as follows. That is, the longest distance calculation unit 151 calculates not only the longest distance but also distances between a plurality of sets of pixels which distances are included in a predetermined range from the longest distance. The sub-pixel generating unit 126 converts the pixels existed in the circumferences of the two pixels forming the distance into the sub-pisels, with regard to all the combinations.

The sub-pixel distance calculation unit 152 performs the process for calculating the distance between the two sub-pixels, on each of the plurality of sets of the two sub-pixels, with regard to all the combinations of one sub-pixel among the plurality of sub-pixels forming the outer circumference of the labeling picture, in the sub-pixel picture of one pixel generated by the sub-pixel generating unit 126, and one sub-pixel among the plurality of sub-pixels forming the outer circumference of the labeling picture in the other sub-pixel picture.

Then, the sub-pixel longest distance calculation unit 153 determines the longest distance of the plurality of distances calculated by the sub-pixel longest distance calculation unit 153, and sends it to the judging unit 125*b*.

This configuration can avoid the occurrence of a situation that the actual distance is not longest even if the distance between the pixels is the longest. Thus, it is possible to determine the true longest distance of the bump 30 in the labeling picture.

(Ninth Embodiment)

A visual inspection apparatus according to the ninth embodiment of the present invention is designed such that the pass or rejection of the inspection of the BGA is judged based on a distance from ae center or a center of gravity in the labeling picture to the outer circumference pixel.

Figure 21:
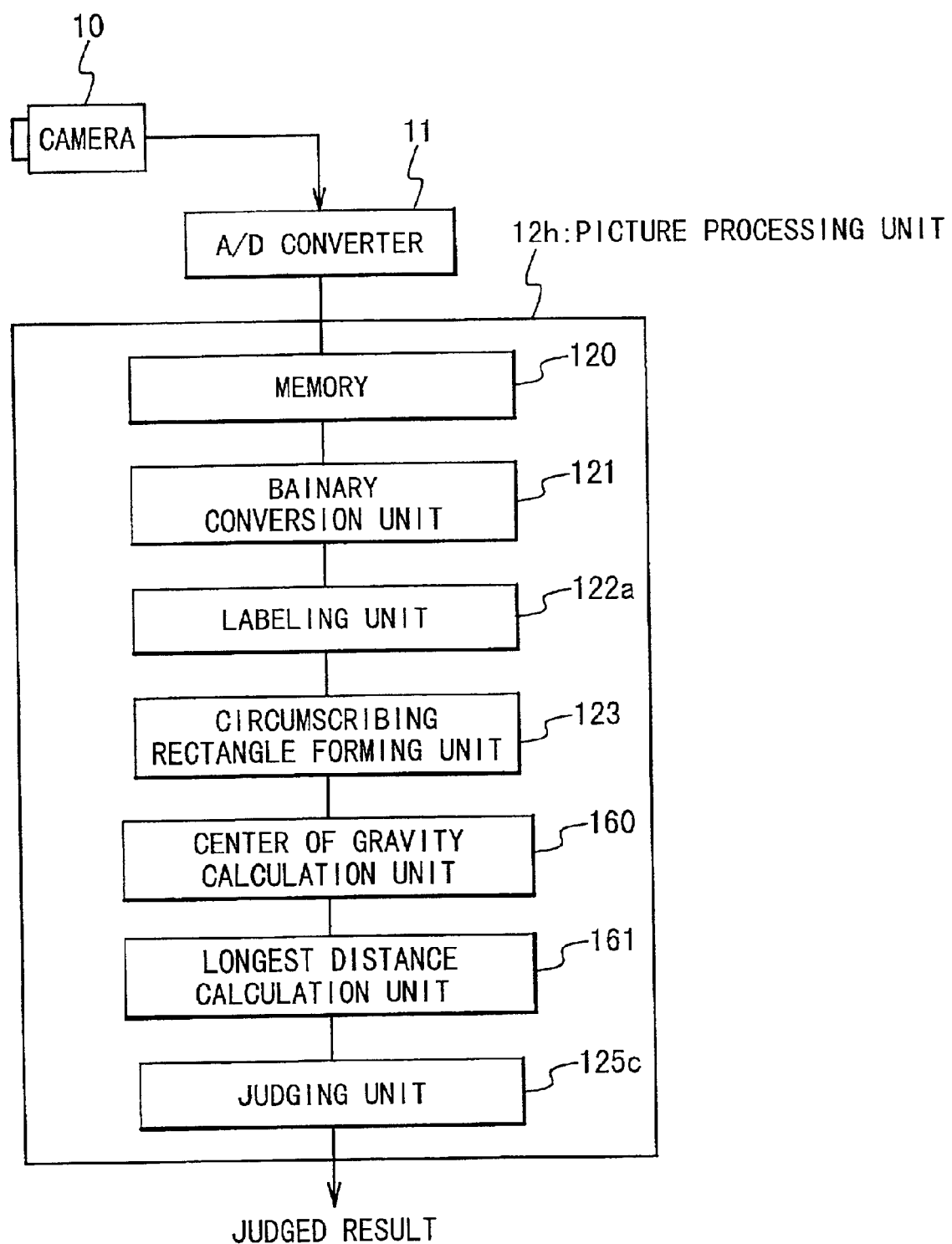
FIG. 21 is a block diagram showing a configuration of a picture processing unit applied to a visual inspection apparatus according to a ninth embodiment of the present invention.

The configuration of a picture processing unit 12*h* of the visual inspection apparatus according to the ninth embodiment is shown in a block diagram of FIG. 21. This visual inspection apparatus is designed such that a center of gravity calculating unit 160 and a longest distance calculation unit 161 are installed instead of the inspection picture generating unit 124 in the first embodiment. The labeling unit 122*a* is identical to that of the second embodiment. Also, the judging unit 125*c* is identical to that of the seventh embodiment.

The center of gravity calculating unit 160 calculates the center of gravity in the labeling picture. The center of gravity may be calculated by using known various methods.

The longest distance calculation unit 161 determines a position of an outer circumference pixel located at the farthest position from the center of gravity, calculates an outer circumference pixel located at the farthest position from the determined position, and sends the determined longest distance to the judging unit 125*c*.

Figure 22:
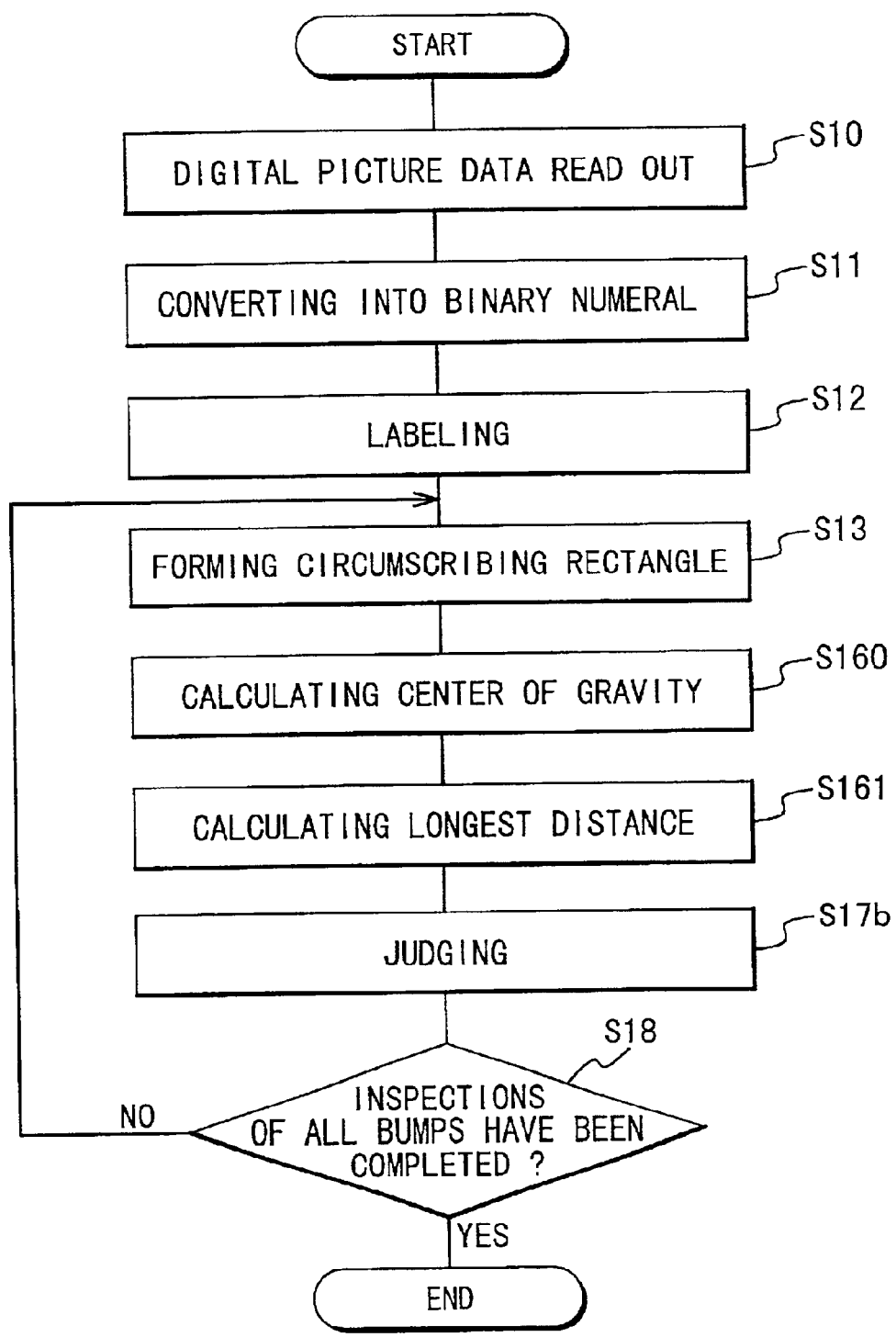
FIG. 22 is a flowchart showing an operation of the visual inspection apparatus according to the ninth embodiment of the present invention.

The operation of the visual inspection apparatus according to the ninth embodiment of the present invention to which the picture processing unit 12*h* having the above-mentioned configuration is applied will be described below with reference to the flowchart shown in FIG. 22.

At first, a photograph of the BGA 20 that is the inspection target sample is taken, and the obtained digital picture data is stored in the memory 120. Then, the digital picture data is read out from the memory 120, and converted into the binary numeral, and labeled. After that, the circumscribing rectangle is formed (Steps S10 to S13). The above-mentioned operations are equal to those of the first embodiment.

Next, the center of gravity is calculated (Step S160). That is, the center of gravity calculating unit 160 calculates the center of gravity, in the labeling picture, as mentioned above.

The longest distance is calculated (Step S161). That is, the longest distance calculation unit 161 determines the position of the outer circumference pixel located at the farthest position from the center of gravity, and calculates the pixel forming the outer circumference located at the farthest position from the determined position.

Then, the pass or rejection of the inspection of the bump 30 is judged (Step S17*b*). That is, it is investigated whether or not the longest distance obtained at the step S151 is within a predetermined range. If the longest distance is within the predetermined range, it is judged as the pass, and if the longest distance is not within the predetermined range, it is judged as the rejection. The judged result is sent to, for example, the external display apparatus (not shown) and displayed thereon.

Next, it is investigated whether or not the inspections of all the bumps 30 have been completed (Step S18). If it is judged that the inspections have not been completed, the operational flow returns back to the step S13, and the above-mentioned processes are carried out, repeatedly. If it is judged at the step S18 that the inspections of all the bumps 30 have been completed, the visual inspection of one BGA 20 is completed.

As mentioned above, in the visual inspection apparatus according to the ninth embodiment of the present invention, it is not necessary to calculate the distance between the two pixels, with regard to all the combinations of the two pixels among the plurality of pixels forming the outer circumference of the labeling picture, as described in the seventh embodiment. Thus, it is possible to attain the high speed processing. In this case, it is impossible to determine the true longest distance such as the seventh embodiment. However, this can sufficiently endure the actual usage condition because the set of the pixels close to the longest distance can be determined.

Also, the center of gravity calculating unit 160 can be replaced by a center calculator for calculating the center of the labeling picture. This center can be calculated by using known various methods. Even this configuration can provide the effects substantially similar to those of the above-mentioned configurations.

It should be noted that a new visual inspection apparatus can be configured by the arbitrary combination of the functions of the visual inspection apparatus of the group composed of the first and second embodiments, the functions of the visual inspection apparatus of the group composed of the third to sixth embodiments, and the functions of the visual inspection apparatus of the group composed of the seventh to ninth embodiments. According to this configuration, it is possible to design the visual inspection apparatus having the higher inspection accuracy including the features of the visual inspection apparatuses of the respective groups.

As detailed above, according to the present invention, it is possible to provide the visual inspection method and the visual inspection apparatus that can carry out the visual inspection at the high accuracy irrespectively of the low cost.

What is claimed is:

1. A visual inspection method comprising:

taking a photograph of an illuminated inspection target sample from above to generate an original picture;

converting said original picture obtained by said taking into a binary picture;

labeling said binary picture obtained by said converting to generate a labeling picture;

forming a circumscribing rectangle circumscribing an outer circumference of said labeling picture obtained by said labeling;

inverting said labeling picture circumscribed by said circumscribing rectangle formed by said forming to generate a inversion picture;

removing a picture in a region surrounded by said outer circumference of said labeling picture and said circumscribing rectangle from said inversion picture obtained by said inverting to generate a removal picture;

adding said removal picture obtained by said removing to said labeling picture to generate an inspection picture; and judging a pass or rejection of said inspection target sample based on said inspection picture obtained by said adding.

2. The visual inspection method according to claim 1, wherein said judging is performed based on at least one of an area of said inspection picture, a diameter of said inspection picture and a circulation degree defined by a ratio of said area to another area calculated by a predetermined equation.

3. The visual inspection method according to claim 2, further comprising:

generating a new inspection picture by converting pixels around a plurality of pixels forming an outer circumference of said inspection picture into sub-pixels, wherein said judging is performed based on said new inspection picture obtained by said generating.

4. The visual inspection method according to claim 3, wherein said original picture obtained by said taking is a picture of a Ball Grid Array (BGA).

5. A visual inspection apparatus comprising:

a camera which takes a photograph of an inspection target sample illuminated with an illuminator from above to output an original picture;

a binary conversion unit which converts said original picture outputted from said camera into a binary picture;

a labeling unit which labels said binary picture outputted from said binary conversion unit to generate a labeling picture;

a circumscribing rectangle forming unit which forms a circumscribing rectangle circumscribing an outer circumference of said labeling picture generated by said labeling unit;

an inspection picture generating unit which generates an inspection picture based on said labeling picture surrounded by said circumscribing rectangle formed by said circumscribing rectangle forming unit; and a judging unit which judges a pass or rejection of said inspection target sample based on said inspection picture generated by said inspection picture generating unit, wherein said inspection picture generating unit comprising:

an inverting unit which inverts said labeling picture circumscribed by said circumscribing rectangle formed by said circumscribing rectangle forming unit to generate a inversion picture;

a removing unit which removes a picture in a region surrounded by said outer circumference and said circumscribing rectangle from said inversion picture generated by said inverting unit to generate a removal picture; and an adding unit which adds said removal picture generated by said removing unit to said labeling picture to generate said inspection picture.

6. The visual inspection apparatus according to claim 5, wherein said judging unit judges said pass or rejection based on at least one of an area of said inspection picture generated by said inspection picture generating unit, a diameter of said inspection picture and a circulation degree defined by a ratio of said area to another area calculated by a predetermined equation.

7. The visual inspection apparatus according to claim 6, further comprising:

a sub-pixel generating unit which converts pixels around a plurality of pixels forming an outer circumference of said inspection picture generated by said inspection picture generating unit into sub-pixels to generate a new inspection picture, wherein said judging unit judges said pass or rejection of said inspection target sample based on said new inspection picture generated by said sub-pixel generating unit.

8. The visual inspection apparatus according to claims 7, wherein said original picture obtained by said camera is a picture of a Ball Grid Array (BGA).

* * * * *